United States Patent
Ohmure et al.

(10) Patent No.: US 11,099,246 B2
(45) Date of Patent: Aug. 24, 2021

(54) MEDICAL IMAGE DIAGNOSIS SYSTEM, MAGNETIC RESONANCE IMAGING APPARATUS, AND IMAGE PROJECTING METHOD

(71) Applicant: Toshiba Medical Systems Corporation, Otawara (JP)

(72) Inventors: Takahiro Ohmure, Otawara (JP); Yu Ueda, Utsunomiya (JP); Kazuya Tanoue, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 446 days.

(21) Appl. No.: 15/268,028

(22) Filed: Sep. 16, 2016

(65) Prior Publication Data
US 2017/0123020 A1    May 4, 2017

(30) Foreign Application Priority Data
Oct. 30, 2015    (JP) .............................. JP2015-214743

(51) Int. Cl.
*G01R 33/28*    (2006.01)
*A61B 5/00*    (2006.01)
(Continued)

(52) U.S. Cl.
CPC .......... *G01R 33/283* (2013.01); *A61B 5/0042* (2013.01); *A61B 5/055* (2013.01);
(Continued)

(58) Field of Classification Search
USPC ....................................................... 600/415
See application file for complete search history.

(56) References Cited

U.S. PATENT DOCUMENTS 5,861,865 A * 1/1999 Anand .................. A61B 5/055
174/350
2003/0085866 A1 * 5/2003 Bimber ................ G05B 19/186
345/156
(Continued)

FOREIGN PATENT DOCUMENTS

JP    10-179543    7/1998
JP    2001-314391    11/2001
(Continued)

OTHER PUBLICATIONS

Machine Translation of JP2014195616A (Year: 2014).*
(Continued)

*Primary Examiner* — Amelie R Davis
*Assistant Examiner* — John Denny Li
(74) *Attorney, Agent, or Firm* — Oblon, McClelland, Maier & Neustadt, L.L.P.

(57) ABSTRACT

A medical image diagnosis system according to one embodiment includes a gantry, a couch, a reflecting plate, and a processing circuitry. The gantry is for medical imaging having a bore. The couch movably supports a top plate. The reflecting plate reflects an image output from an image output device. The processing circuitry, in a first case where the image is shown to an observer not through the reflecting plate, outputs a first image signal relating to a first image to the image output device. While in a second case where the image is shown to the observer through the reflecting plate, The processing circuitry outputs a second image signal relating to a second image to the image output device.

7 Claims, 20 Drawing Sheets

(51) Int. Cl.
*A61B 5/055* (2006.01)
*G01R 33/30* (2006.01)
*G01R 33/36* (2006.01)
*G01R 33/385* (2006.01)
*G01R 33/56* (2006.01)

(52) U.S. Cl.
CPC ........... *G01R 33/307* (2013.01); *G01R 33/36* (2013.01); *G01R 33/385* (2013.01); *G01R 33/56* (2013.01)

(56) References Cited

U.S. PATENT DOCUMENTS

| | | | | |
|---|---|---|---|---|
| 2006/0247521 | A1* | 11/2006 | McGee | A61B 5/0071 600/434 |
| 2013/0051755 | A1* | 2/2013 | Brown | H04N 21/4532 386/241 |
| 2013/0218004 | A1* | 8/2013 | Yang | G01R 33/283 600/415 |
| 2013/0235168 | A1* | 9/2013 | Gillies | A61B 5/055 348/51 |
| 2015/0031984 | A1* | 1/2015 | Driemel | G01R 33/283 600/415 |
| 2017/0020409 | A1* | 1/2017 | Hengerer | G16H 40/63 |
| 2017/0119320 | A1 | 5/2017 | Ueda et al. | |
| 2017/0123021 | A1 | 5/2017 | Takamori et al. | |

FOREIGN PATENT DOCUMENTS

| | | | |
|---|---|---|---|
| JP | 2013-546024 | | 12/2013 |
| JP | 2014-195616 | | 10/2014 |
| JP | 2014195616 A | * | 10/2014 |
| JP | 2014-212945 | | 11/2014 |
| JP | 2017-80298 A | | 5/2017 |
| JP | 2017-80299 A | | 5/2017 |

OTHER PUBLICATIONS

Japanese Office Action dated Jul. 9, 2019 in Japanese Application No. 2015-214743, citing document AO therein, 4 pages.

\* cited by examiner

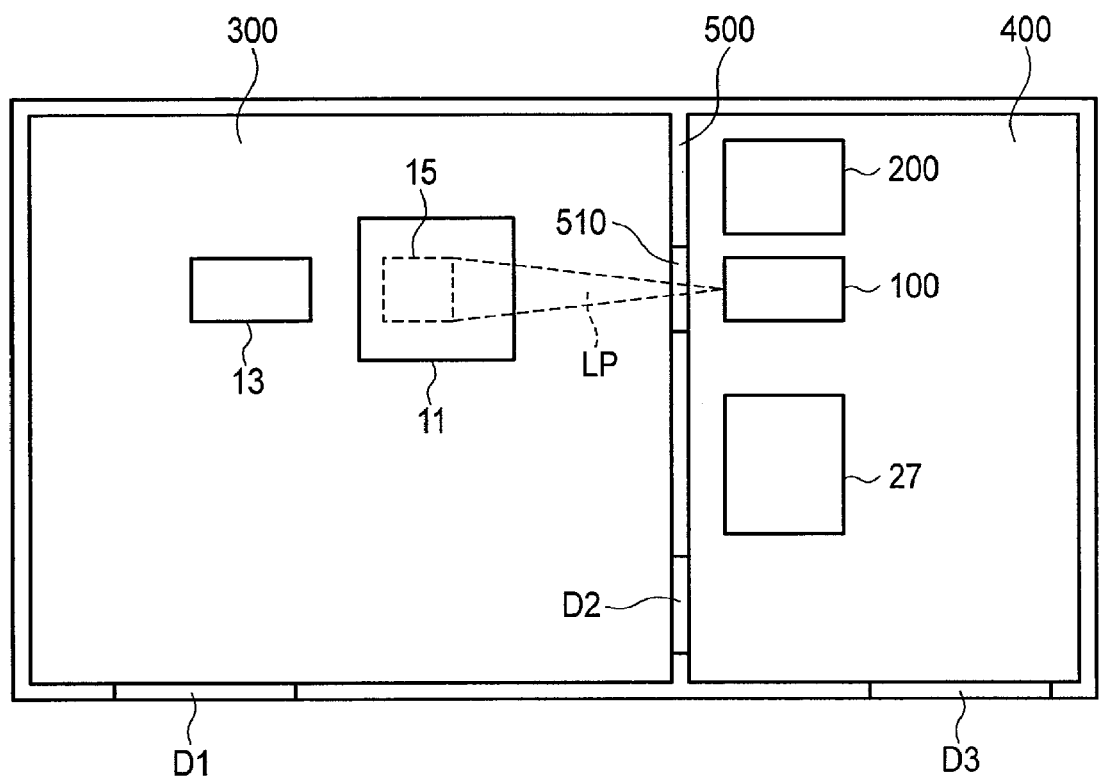
F I G. 3

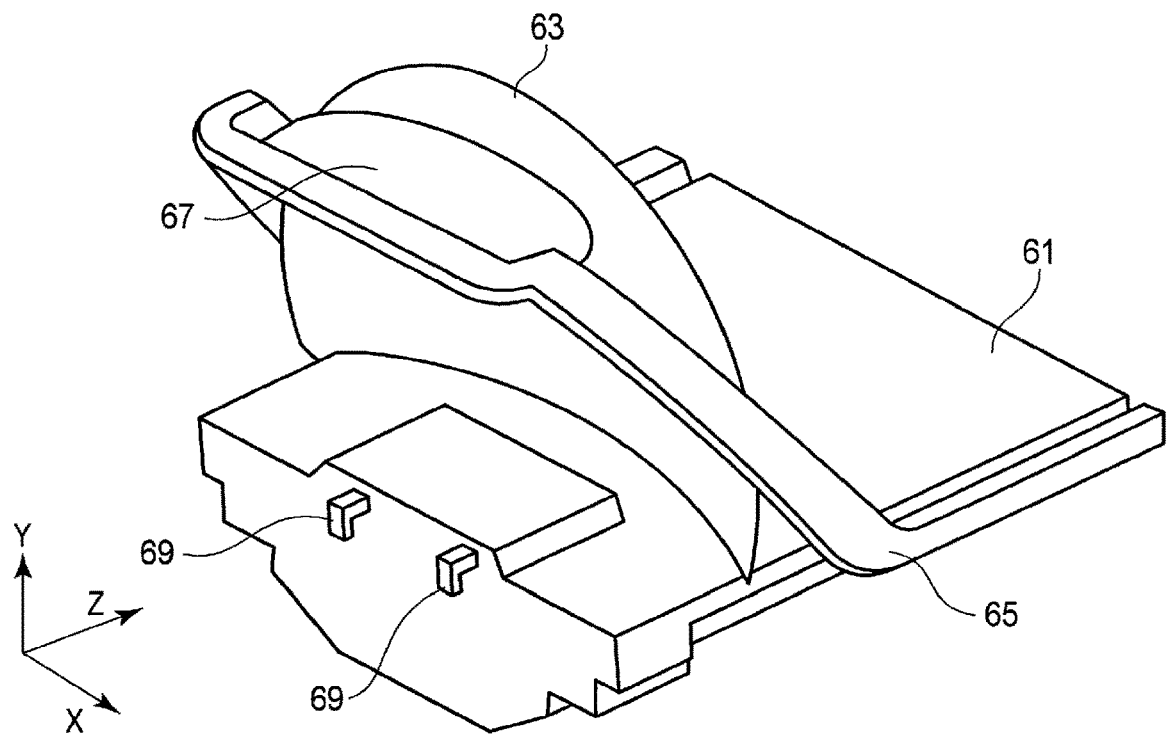
F I G. 5
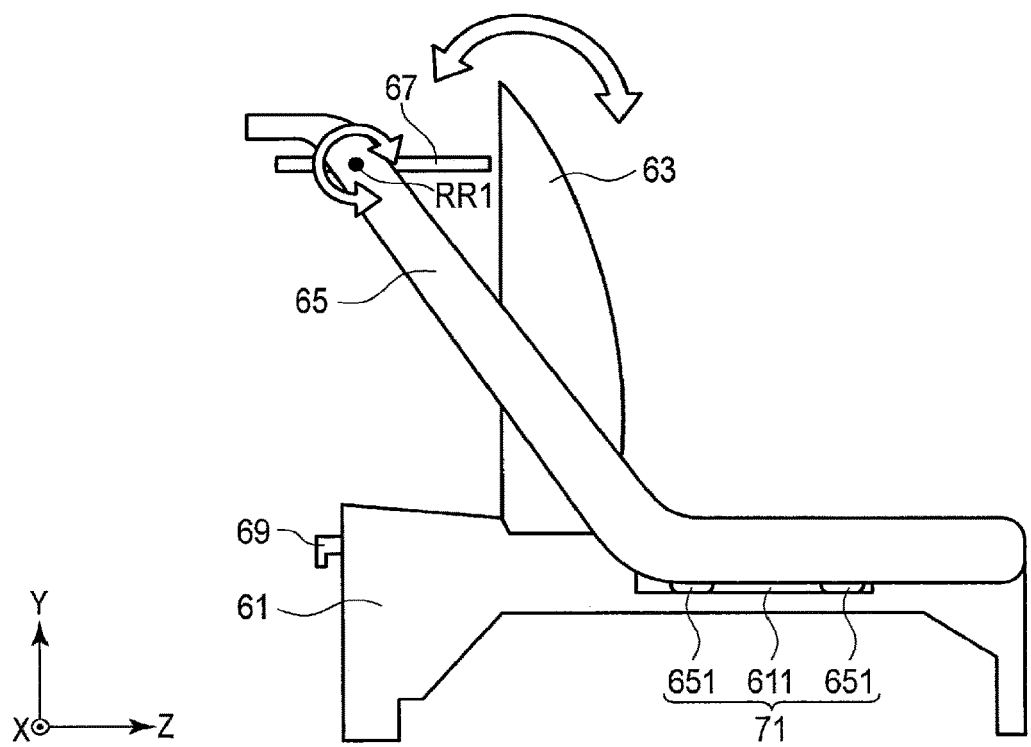
F I G. 6

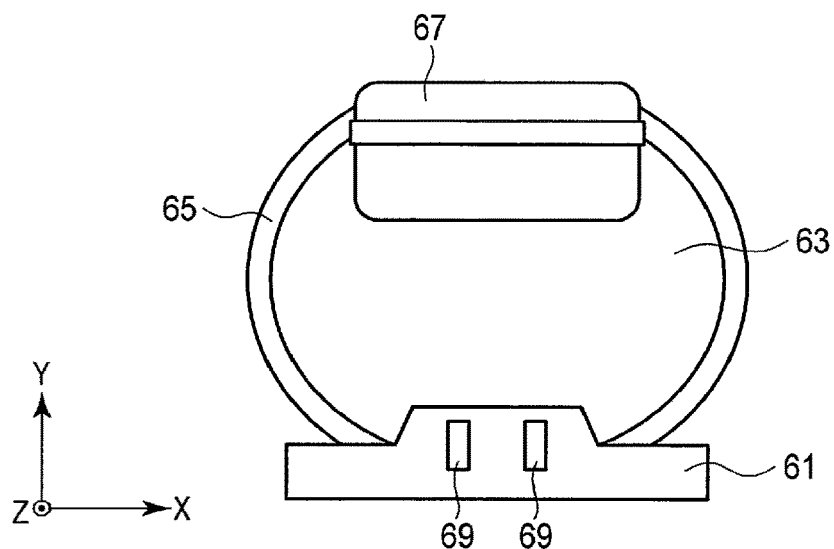
F I G. 7
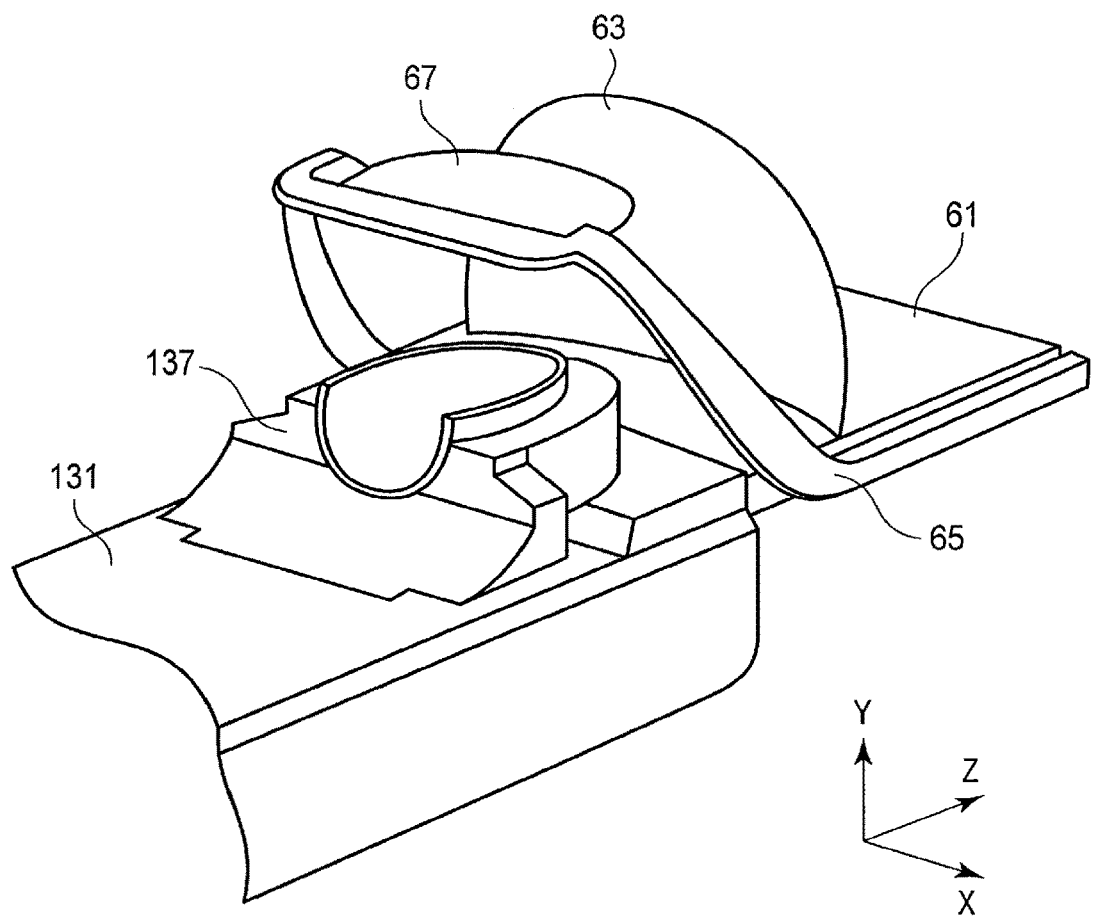
F I G. 8

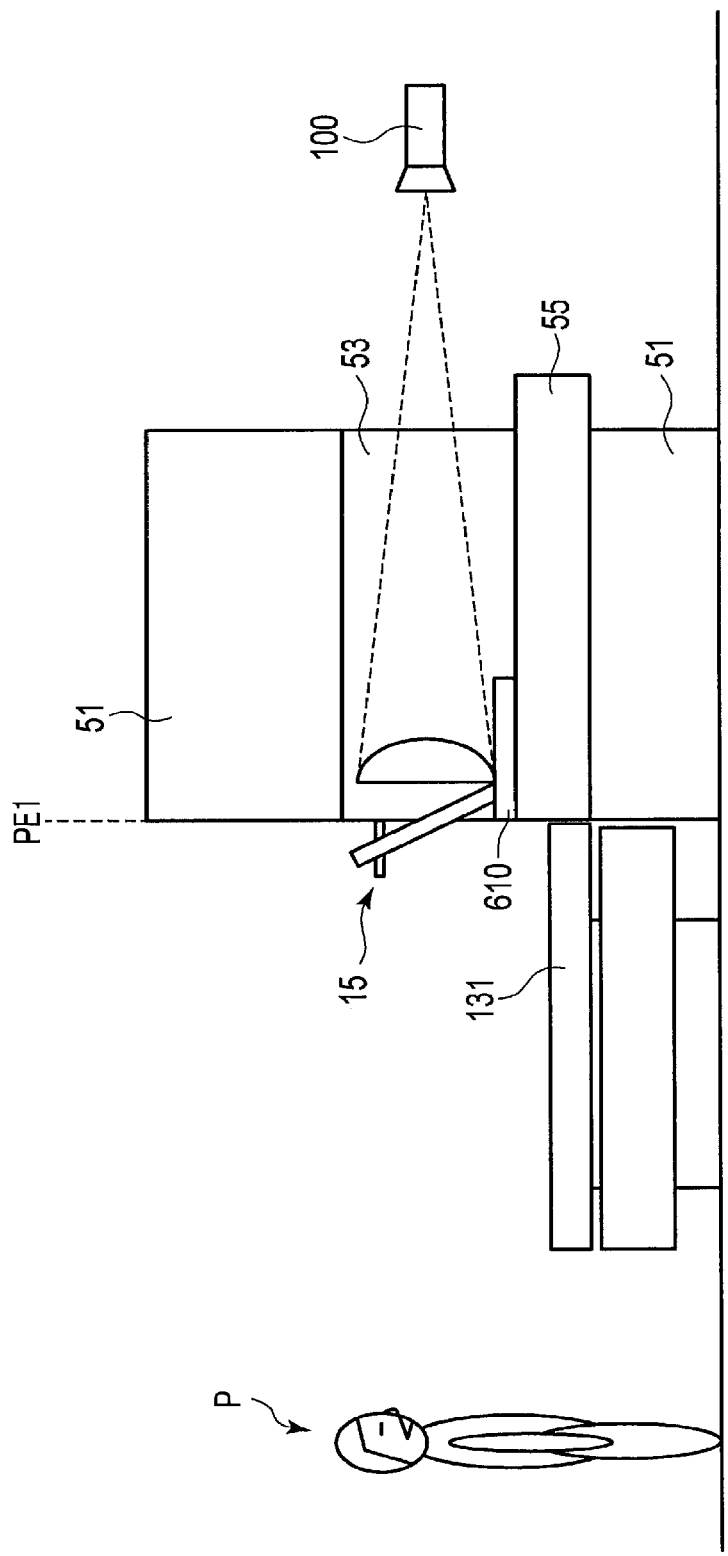
F I G. 12

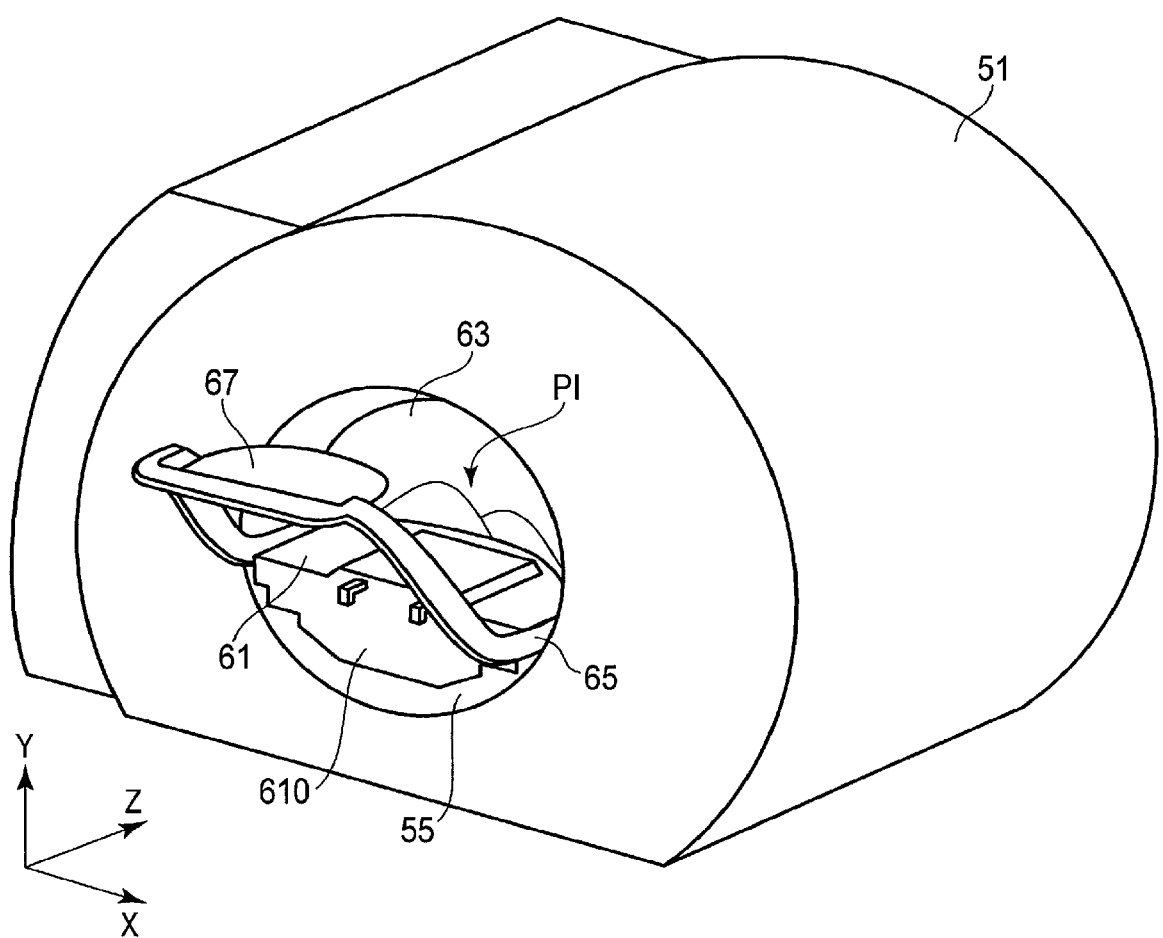
F I G. 13

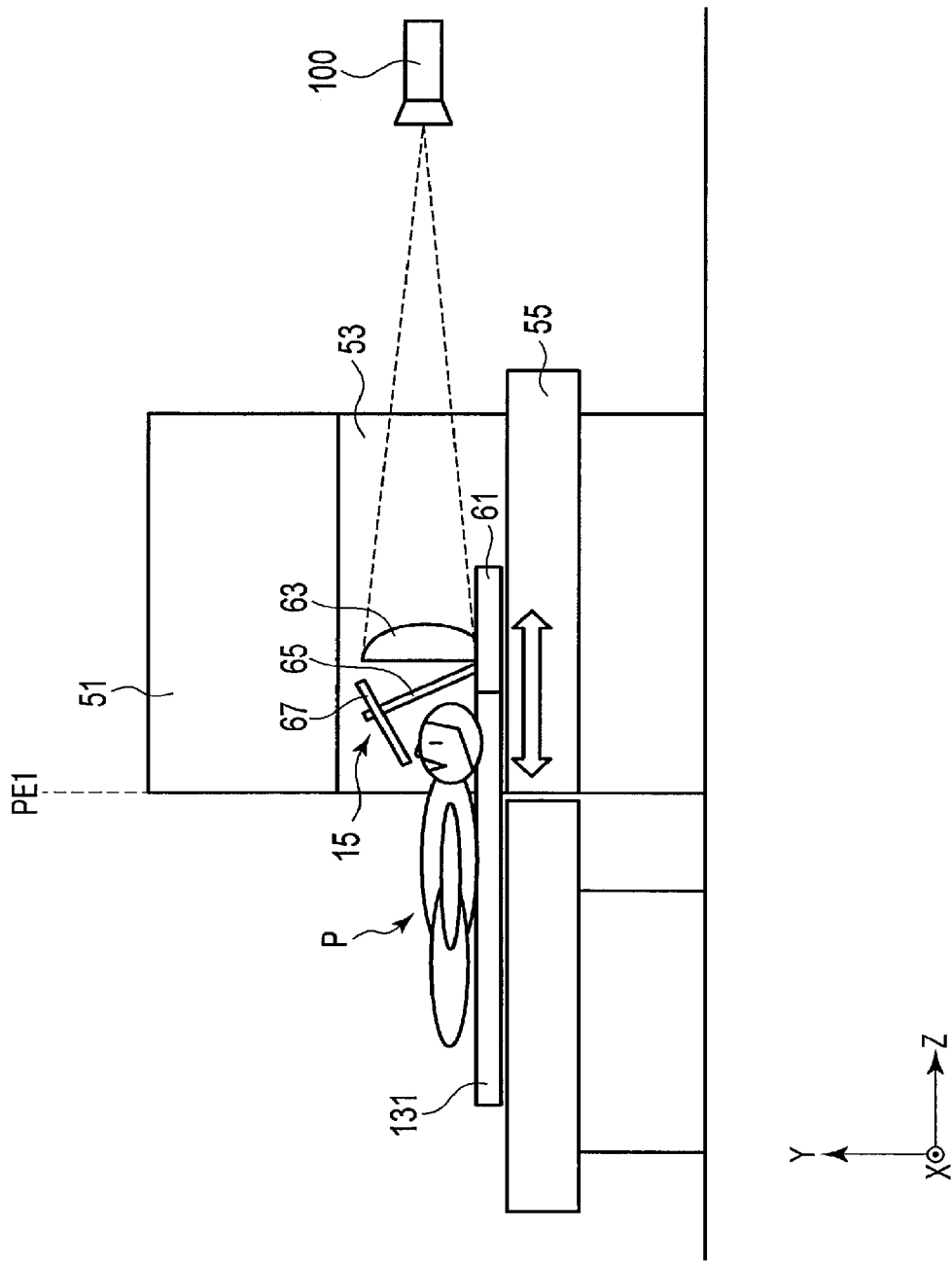
F I G. 14

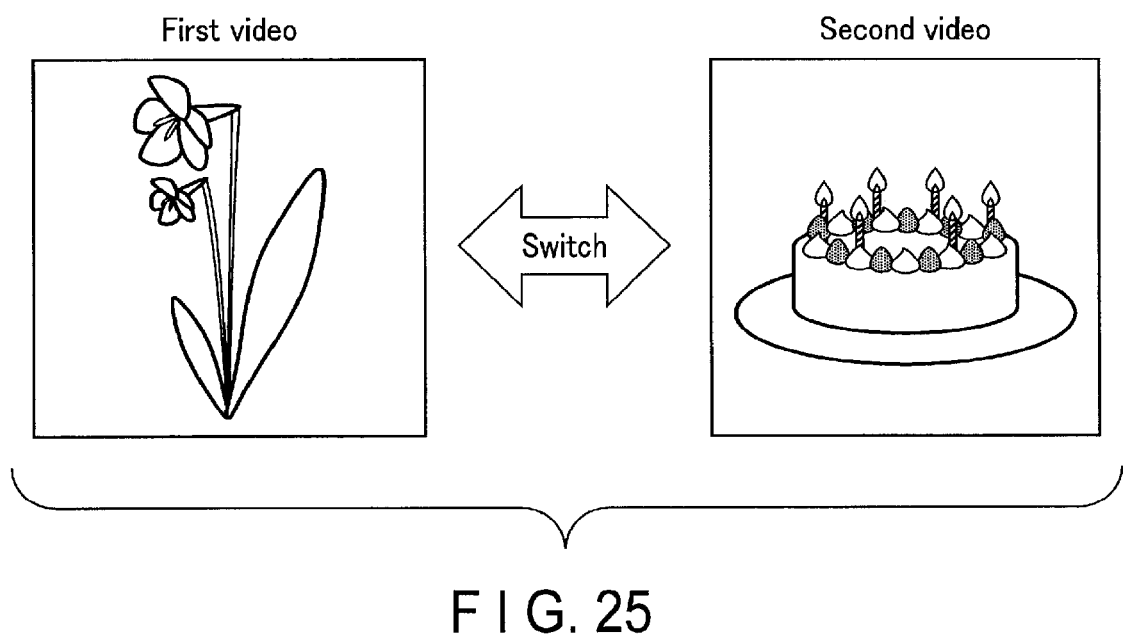
F I G. 25

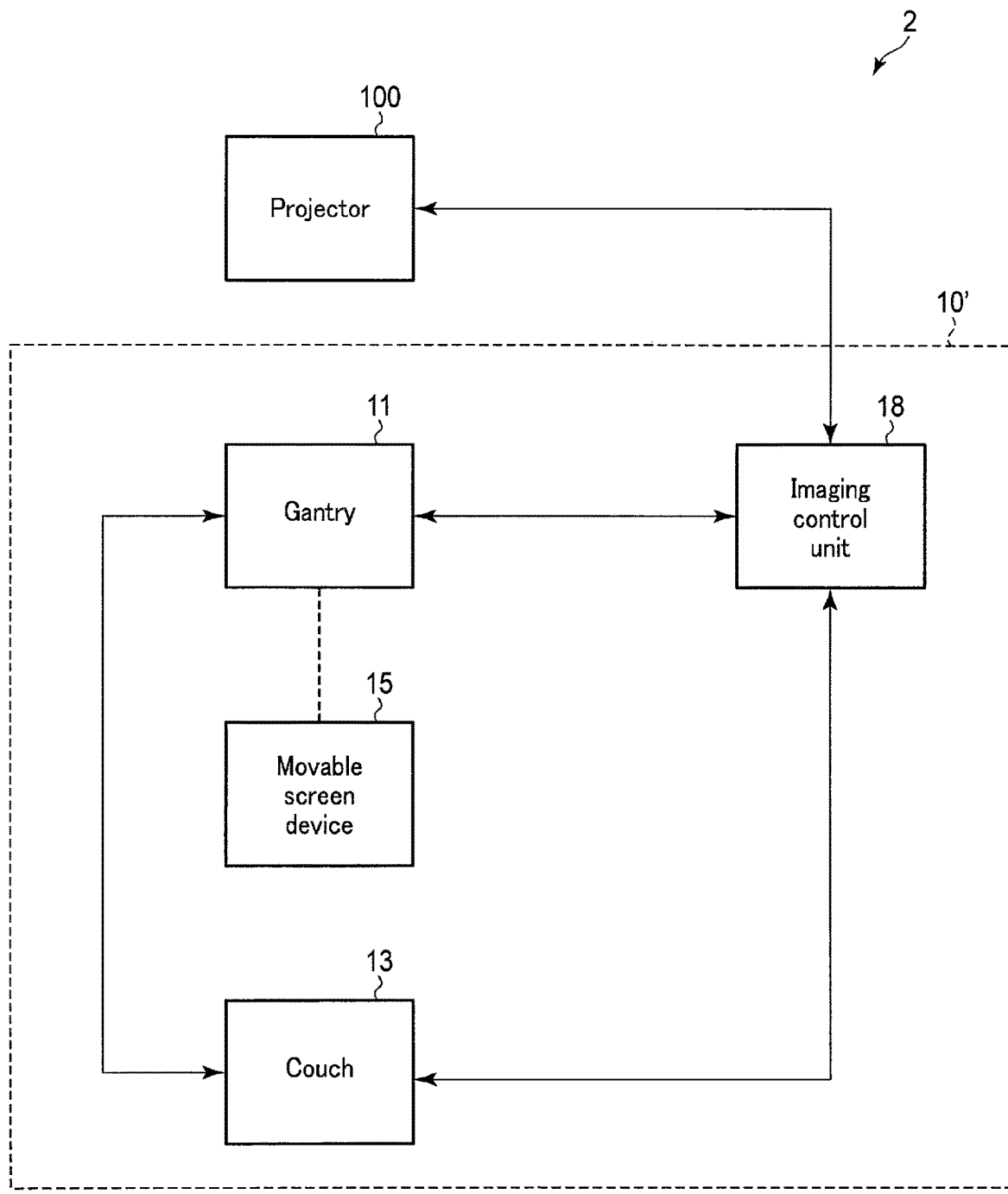
F I G. 26

MEDICAL IMAGE DIAGNOSIS SYSTEM, MAGNETIC RESONANCE IMAGING APPARATUS, AND IMAGE PROJECTING METHOD

CROSS-REFERENCE TO RELATED APPLICATIONS

This application is based upon and claims the benefit of priority from prior Japanese Patent Application No. 2015-214743, filed Oct. 30, 2015, the entire contents of which are incorporated herein by reference.

FIELD

Embodiments described herein relate generally to a medical image diagnosis system, a magnetic resonance imaging apparatus, and an image projecting method.

BACKGROUND

A magnetic resonance imaging apparatus has a gantry on which an imaging mechanism such as a magnet is attached. A substantially hollow-shaped bore is formed in the gantry. MR (Magnetic Resonance) imaging is performed in a state where a patient is inserted into the bore. A gantry having a relatively large bore diameter has been developed, but not a few patients feel stress by an MR examination due to a long MR imaging time, a noise while the gantry is being driven, and a sense of pressure and a locked up feeling in the bore.

BRIEF DESCRIPTION OF THE DRAWING

FIG. 3 is a diagram illustrating an example of an installation environment of a magnetic resonance imaging system according to the embodiment;

FIG. 5 is a perspective view of a movable screen unit according to the embodiment;

FIG. 6 is a side view of the movable screen unit in FIG. 5;

FIG. 7 is a front view of the movable screen unit in FIG. 5;

FIG. 8 is a perspective view of the connected movable screen unit and a top plate according to the embodiment;

FIG. 12 is a diagram of the movable screen unit in a first projection mode illustrated from a side of the gantry;

FIG. 13 is a diagram of the movable screen unit in the first projection mode illustrated from a front of the gantry;

FIG. 14 is a diagram of the movable screen unit in a second projection mode illustrated from a side of the gantry;

FIG. 25 is a view schematically illustrating the first video and the second video relating to a different content;

FIG. 26 is a diagram illustrating configuration of a magnetic resonance imaging system according to a variation.

DETAILED DESCRIPTION

A medical image diagnosis system according to this embodiment has a gantry, a couch, a reflecting plate, and a processing circuit. The gantry is a gantry for medical imaging having a bore. The couch movably supports a top plate. The reflecting plate reflects an image output from an image output device. The processing circuit, in a first case where the image is shown to an observer not through the reflecting plate, output a first image signal relating to a first image to the image output device, while in a second case where the image is shown to the observer through the reflecting plate, output a second image signal relating to a second image to the image output device.

The following technique can be considered for alleviating stress in an MR examination. For example, there are: 1. a goggle-type head-mount display; 2. installation of a liquid crystal monitor on a ceiling or a wall of an examination room; and 3. a head coil to which a mirror for seeing an image on a liquid crystal monitor disposed on a rear of the gantry is mounted. However, in the case of the technique 1, mounting the head-mount display gives a patient a sense of pressure or a locked up feeling. In the case of the technique 2, when the head part of the patient enters the gantry, the image on the liquid crystal monitor cannot be seen. In the case of the technique 3, the image can be seen through the mirror attached to the head coil during MR imaging, the locked up feeling by the bore can be alleviated. However, the mirror needs to be mounted on each head coil. Moreover, since the mirror is mounted on a gap of the head coil covering the head part, the patient cannot feel expansion of the image very much. Moreover, since the liquid crystal monitor is installed on the rear of the gantry and does not hide a front of the gantry, the patient can visually recognize the bore easily when being outside the gantry before the MR imaging and even if the patient wears the head coil and sees the image through the mirror after that, a feeling of being inside the bore cannot be wiped off. Furthermore, since a position relation between the mirror and the liquid crystal monitor is changed with movement of the top plate, even if the patient is seeing the image on the liquid crystal monitor through the mirror during movement of the top plate, a feeling of advancing in the bore remains in the patient.

Hereinafter, a medical image diagnosis system, a magnetic resonance imaging device, and an image projecting method according to an embodiment will be described by referring to the attached drawings.

Figure 1:
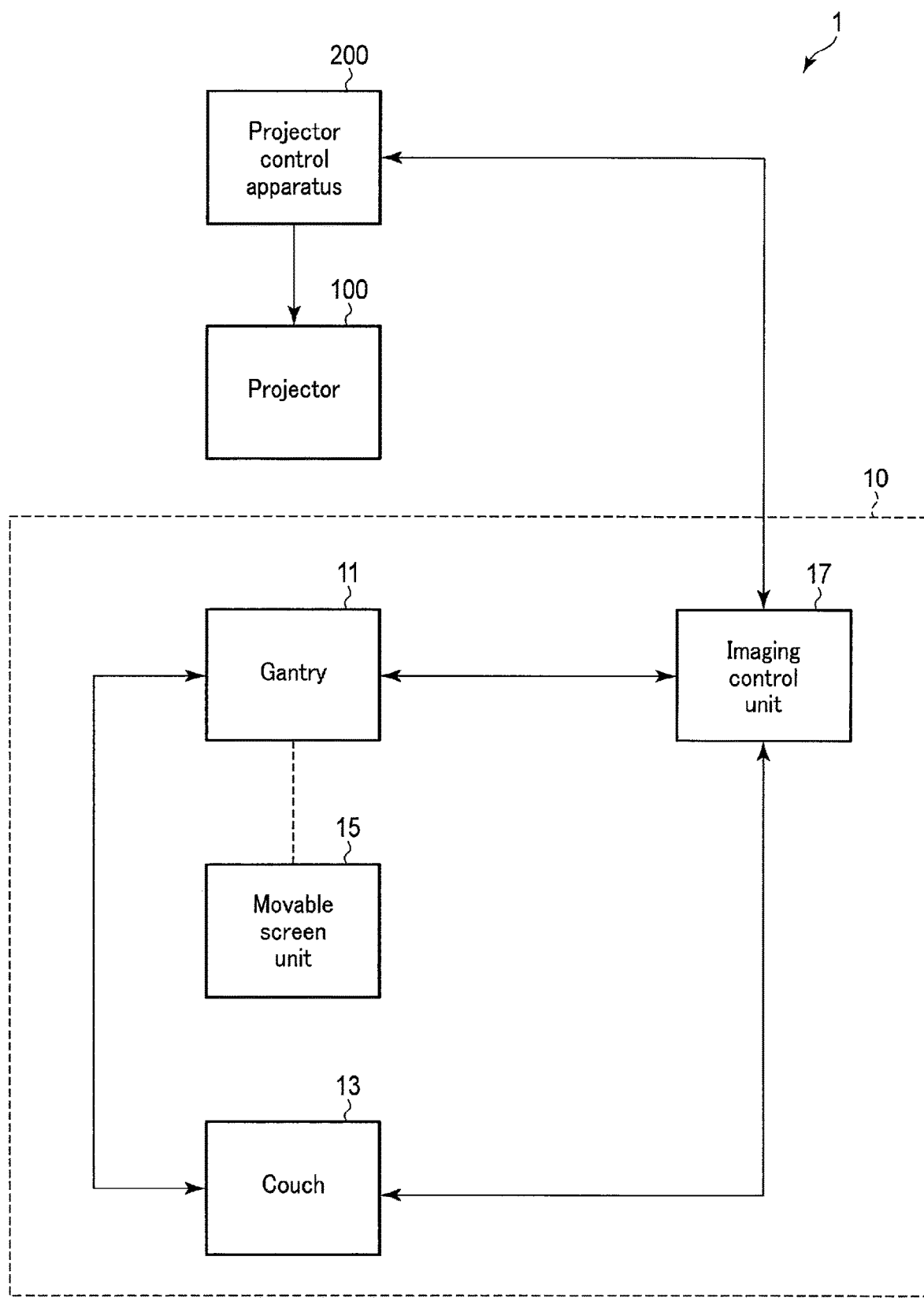
FIG. 1 is a diagram illustrating configuration of a medical image diagnosis system according to an embodiment.

FIG. 1 is a diagram illustrating configuration of the medical image diagnosis system 1 according to this embodiment. As illustrated in FIG. 1, the medical image diagnosis system 1 includes a medical image diagnosis apparatus 10, a projector 100, and a projector control apparatus 200 communicably connected to each other via wire or wirelessly. The medical image diagnosis apparatus 10 has a gantry 11, a couch 13, a movable screen unit 15, and an imaging control unit 17. The gantry 11, the couch 13, and the movable screen unit 15 are installed in an examination room, for example, and the imaging control unit 17 is installed in a control room adjacent to the examination room. The gantry 11 is equipped with a mechanism for realizing medical imaging. A bore having a hollow shape is formed in the gantry 11. The couch 13 is installed in front of the gantry 11. The couch 13 movably supports a top plate on which a patient is placed. The couch 13 moves the top plate in accordance with control by the gantry 11, the imaging control unit 17 and the like. In the bore of the gantry 11, the movable screen unit 15 is movably provided. In front or rear of the gantry 11, the projector 100 is installed. On the movable screen unit 15, an image from the projector 100 is projected.

The projector control apparatus 200 is a computer device controlling the projector 100. The projector control apparatus 200 supplies an image signal of a projection target to the projector 100. The projector 100 projects a image corresponding to the image signal from the projector control apparatus 200 on a screen of the movable screen unit 15. As the projector 100, a liquid crystal method, a DLP (Digital Light Processing) method, a LCOS (Liquid Crystal On Silicon) method, a GLV (Grating Light Valve) method and the like are favorably used. In this case, the projector 100 has at least a display device and a light source mounted thereon. The display device displays the image corresponding to the image signal from the projector control apparatus 200. The light source irradiates light to the display device directly or indirectly via an optical system. The light transmitted or reflected from the display device (hereinafter referred to as projected light) is emitted to an outside of the projector 100 directly or indirectly via the optical system. By irradiating the projected light to the movable screen unit 15, the image corresponding to the projected light is projected on the movable screen unit 15.

The imaging control unit 17 functions as a center of the medical image diagnosis apparatus 10. For example, the imaging control unit 17 controls the gantry 11 for performing medical imaging. The imaging control unit 17 reconstructs a medical image relating to a patient P based on raw data collected by the gantry 11 in the medical imaging. The imaging control unit 17 may be configured controllable of the projector 100 via the projector control apparatus 200.

The medical image diagnosis system 1 according to this embodiment enables improvement of habitability in the bore during medical imaging by the medical image diagnosis apparatus 10, by using the projector 100 and the movable screen unit 15. As the medical image diagnosis apparatus 10 according to this embodiment, any device capable of imaging the patient P using the gantry 11 in which the bore is formed can be used. Specifically, the medical image diagnosis apparatus 10 according to this embodiment can be applied to single modality such as an MRI (Magnetic Resonance Imaging) apparatus, a CT (Computed Tomography) apparatus, a PET (Positron Emission Tomography) apparatus, and a SPECT (Single Photon Emission Computed Tomography) apparatus and the like. Alternatively, the medical image diagnosis apparatus 10 according to this embodiment may be applied to multi-modality such as an MR/PET apparatus, a CT/PET apparatus, an MR/SPECT apparatus, a CT/SPECT apparatus and the like. However, in order to make specific explanation below, the medical image diagnosis apparatus 10 according to this embodiment is assumed to be the magnetic resonance imaging apparatus 10. Moreover, the medical image diagnosis system 1 including the magnetic resonance imaging apparatus 10, the projector 100, and the projector control apparatus 200 shall be called the magnetic resonance imaging system 1.

Figure 2:
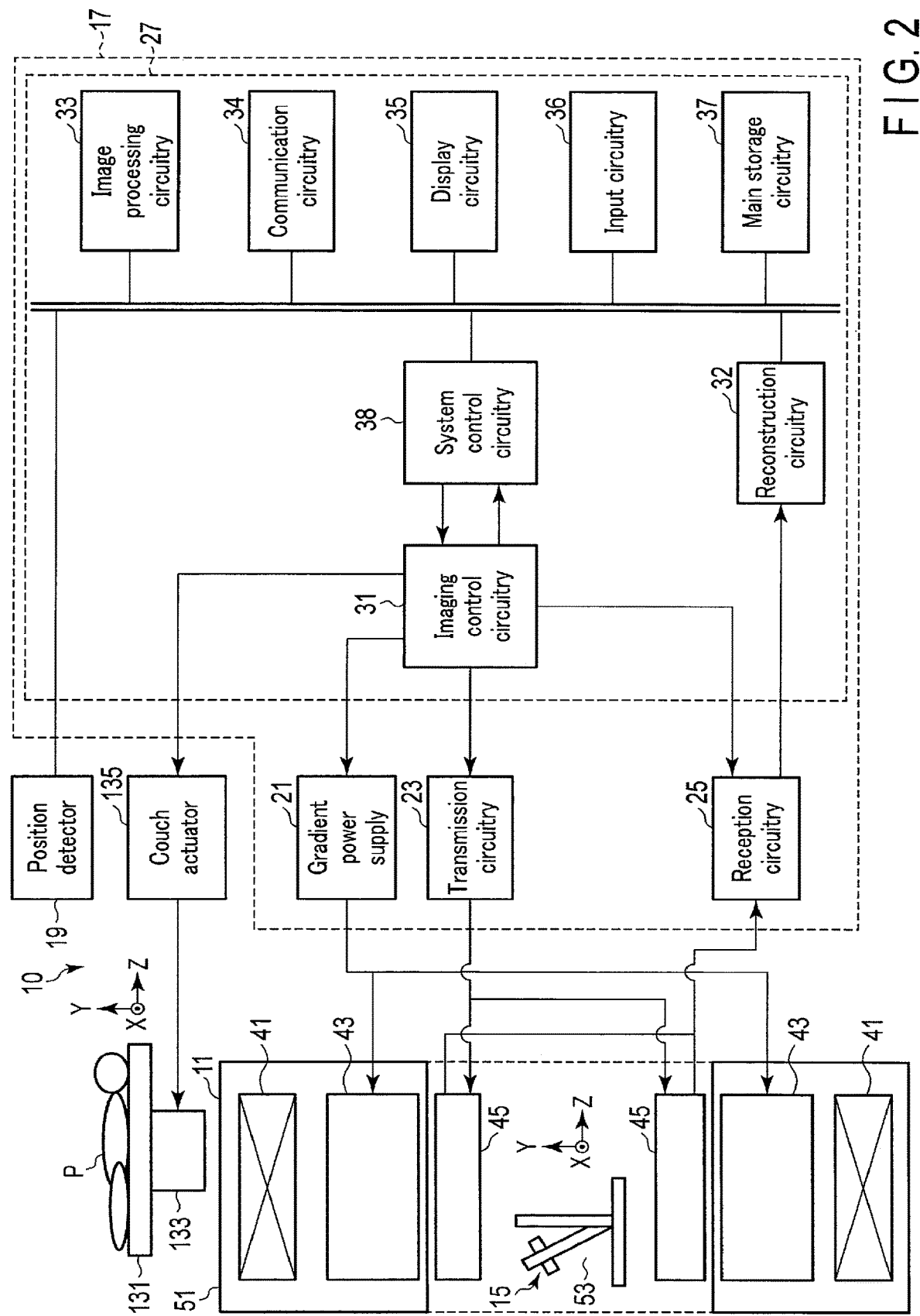
FIG. 2 is a diagram illustrating configuration of a magnetic resonance imaging apparatus according to the embodiment.

FIG. 2 is a diagram illustrating configuration of the magnetic resonance imaging apparatus 10 according to this embodiment. As illustrated in FIG. 2, the magnetic resonance imaging apparatus 10 has the gantry 11, the couch 13, the movable screen unit 15, the imaging control unit 17, and a position detector 19. The imaging control unit 17 has a gradient power supply 21, a transmission circuitry 23, a reception circuitry 25, and a console 27. The console 27 has an imaging control circuitry 31, a reconstruction circuitry 32, an image processing circuitry 33, a communication circuitry 34, a display circuitry 35, an input circuitry 36, a main storage circuitry 37, and a system control circuitry 38. The imaging control circuitry 31, the reconstruction circuitry 32, the image processing circuitry 33, the communication circuitry 34, the display circuitry 35, the input circuitry 36, the main storage circuitry 37, and the system control circuitry 38 are communicably connected to each other via a bus. The gradient power supply 21, the transmission circuitry 23, and the reception circuitry 25 are provided separately from the console 27 and the gantry 11.

The gantry 11 has a static field magnet 41, a gradient coil 43, and an RF coil 45. The static field magnet 41 and the gradient coil 43 are contained in a housing (hereinafter referred to as a gantry housing) 51 of the gantry 11. In the gantry housing 51, a bore 53 having a hollow shape is formed. The RF coil 45 is disposed in the bore 53 of the gantry housing 51. The movable screen unit 15 according to this embodiment is disposed in the bore 53 of the gantry housing 51.

The static field magnet 41 has a hollow and substantially cylindrical shape and generates a static field in the substantially cylinder. As the static field magnet 41, a permanent magnet, a superconductive magnet or a resistive magnet or the like is used, for example. Here, a center axis of the static field magnet 41 is specified as a Z-axis, an axis vertically orthogonal to the Z-axis is called a Y-axis, and an axis horizontally orthogonal to the Z-axis is called an X-axis. The X-axis, the Y-axis, and the Z-axis constitute an orthogonal three-dimensional coordinate system.

The gradient coil 43 is a coil unit formed having a hollow and substantially cylindrical shape mounted on the inner side of the static field magnet 41. The gradient coil 43 generates a gradient magnetic field upon receipt of supply of the electric current from the gradient power supply 21.

A gradient power supply 21 supplies the electric current to the gradient coil 43 in accordance with control by the imaging control circuitry 31. The gradient power supply 21 generates the gradient magnetic field in the gradient coil 43 by supplying the electric current to the gradient coil 43.

The RF coil 45 is disposed on the inner side of the gradient coil 43 and generates a high-frequency magnetic field upon receipt of supply of the RF pulse from the transmission circuitry 23. The RF coil 45 receives a magnetic resonance signal (hereinafter referred to as an MR signal) generated from a target atomic nucleus present in the patient P upon receipt of an action of the high-frequency magnetic field. The received MR signal is supplied to the reception circuitry 25 via wire or wirelessly. The aforementioned RF coil 45 is assumed to be a coil having a transmission/reception function, but an RF coil for transmission and an RF coil for reception may be provided separately.

The transmission circuitry 23 transmits the high-frequency magnetic field to the patient P through the RF coil 45 for exciting the target nucleus atom present in the patient P. As the target nucleus atom, proton is used typically. Specifically, the transmission circuitry 23 supplies a high-frequency signal (RF signal) for exciting the target nucleus atom to the RF coil 45 in accordance with control by the imaging control circuitry 31. The high-frequency magnetic field generated from the RF coil 45 oscillates at a resonance frequency specific to the target nucleus atom and excites the target nucleus atom. The MR signal is generated from the excited target nucleus atom and is detected by the RF coil 45. The detected MR signal is supplied to the reception circuitry 25.

The reception circuitry 25 receive the MR signal generated from the excited target nucleus atom through the RF coil 45. The reception circuitry 25 generates a digital MR signal by executing signal processing of the received MR signal. The digital MR signal is supplied to the reconstruction circuitry 32 via wire or wirelessly.

The couch 13 is installed adjacent to the gantry 11. The couch 13 has a top plate 131 and a base 133. The patient P is placed on the top plate 131. The base 133 slidably supports the top plate 131 along each of the X-axis, the Y-axis, and the Z-axis. A couch actuator 135 is accommodated in the base 133. The couch actuator 135 moves the top plate 131 upon control from the imaging control circuitry 31. As the couch actuator 135, any motor such as a servo motor, a stepping motor and the like may be also used.

The position detector 19 detects positions of various devices included in the magnetic resonance imaging system 1. The device whose position is to be detected may be any of the gantry 11, the couch 13, the movable screen unit 15 and other devices. For example, the position detector 19 detects positions of various devices such as the top plate 131 included in the couch 13 or the movable screen unit 15, a movable truck 61, a screen 63, a support arm 65, a reflecting plate 67 and the like and outputs a digital electric signal relating to the detected position (hereinafter referred to as a position signal). It is assumed that the position detected by the position detector 19 includes not only the position itself but also an angle, a distance or a movement amount specifying the position and an index such as presence of detection of the device by the position detector 19. Any position detector 19 can be used as long as it can detect the aforementioned positions. For example, a position sensor, a distance sensor, a displacement sensor, a pressure sensor, a speed sensor, a photo sensor, an ultrasonic sensor and the like can be used as the position detector 19. The position signal is supplied to the console 27 via wire or wirelessly and is supplied to the projector control apparatus 200 by the communication circuitry 34 of the console 27. Alternatively, the position signal may be supplied to the projector control apparatus 200 not through the console 27.

The imaging control circuitry 31 has a processor such as a CPU (Central Processing Unit) and an MPU (Micro Processing Unit) and a memory such as a ROM (Read Only Memory) and a RAM (Random Access Memory) as hardware resources. The imaging control circuitry 31 synchronously controls the gradient power supply 21, the transmission circuitry 23, and the reception circuitry 25 based on pulse sequence information supplied from the system control circuitry 38 and performs an MR imaging for the patient P in a pulse sequence according to the pulse sequence information.

The reconstruction circuitry 32 has a processor such as a CPU, a GPU (Graphical processing unit), an MPU and a memory such as a ROM and a RAM as hardware resources. The reconstruction circuitry 32 reconstructs an MR image relating to the patient P based on the MR signal from the reception circuitry 25. For example, the reconstruction circuitry 32 applies Fourier transform or the like to the MR signal disposed in a k-space or in a frequency space and generates an MR image defined in a real space. The reconstruction circuitry 32 may be also constituted by an Application Specific Integrated Circuit (ASIC) or a Field Programmable Logic Device (FPGA) realizing a reconstruction function and other Complex Programmable Logic Device (CPLD), and a Simple Programmable Logic Device (SPLD).

The image processing circuitry 33 has a processor such as a CPU, a GPU, and an MPU and a memory such as a ROM and a RAM as hardware resources. The image processing circuitry 33 applies various types of image processing to the MR image reconstructed by the reconstruction circuitry 32. The image processing circuitry 33 may be constituted by the ASIC, FPGA, CPLD, and SPLD realizing the aforementioned image processing function.

The communication circuitry 34 conducts data communication with the projector control apparatus 200 via wire, not shown, or wirelessly. The communication circuitry 34 may also conduct data communication with an external device such as a PACS server connected through a network or the like, not shown. The communication circuitry 34 may supply the position signal supplied from the position detector 19 to projector control apparatus 200.

The display circuitry 35 displays various types of information. For example, the display circuitry 35 displays the MR image reconstructed by the reconstruction circuitry 32 or the MR image to which imaging processing is applied by the image processing circuitry 33. The display circuitry 35 may also display the same image as the image projected by the projector 100. Specifically, the display circuitry 35 has a display interface circuit and a display device. The display interface circuit converts data representing a display target to an image signal. A display signal is supplied to the display device. The display device displays the image signal representing a display target. As the display device, a CRT display, a liquid crystal display, an organic EL display, an LED display, a plasma display or any other arbitrary display known in this technical field can be used as appropriate.

The input circuitry 36 specifically has an input device and an input interface circuit. The input device receives various instructions from a user. As the input device, a keyboard, a mouse and a various switches can be used. The input interface circuit supplies an output signal from the input device to the system control circuitry 38 through a bus. The input circuitry 36 is not limited to those provided with physical operation components such as a mouse and a keyboard. For example, a processing circuit of an electric signal which receives the electric signal corresponding to an input operation from an external input device provided separately from the magnetic resonance imaging apparatus 10 and outputs the received electric signal to various circuits is also included in an example of the input circuitry 36.

The main storage circuitry 37 is a storage device such as an HDD (hard disk drive), an SSD (solid state drive), and an integrated circuit storage device storing various types of information. The main storage circuitry 37 may be a CD-ROM drive, a DVD drive, and a driving device for reading/writing various types of information with portable storage medium such as a flash memory. For example, the main storage circuitry 37 stores the MR image, a control program of the magnetic resonance imaging apparatus 10.

The system control circuitry 38 has a processor such as a CPU or an MPU and a memory such as a ROM and a RAM as hardware resources. The system control circuitry 38 functions as a center of the magnetic resonance imaging apparatus 10. Specifically, the system control circuitry 38 reads out the control program stored in the main storage circuitry 37, expand it on the memory, and control each part of the magnetic resonance imaging apparatus 10 in accordance with the expanded control program.

The magnetic resonance imaging apparatus 10 of this embodiment will be described below in detail.

First, by referring to FIG. 3, an installation environment of the magnetic resonance imaging system 1 according to this embodiment will be described. FIG. 3 is a diagram illustrating an example of the installation environment of the magnetic resonance imaging system according to this embodiment. As illustrated in FIG. 3, an examination room 300 where the MR imaging is performed and a control room 400 adjacent to the examination room 300 are provided. In the examination room 300, the gantry 11 and the couch 13 are installed. In front of the gantry 11, the couch 13 is provided. The movable screen unit 15 is provided in the bore of the gantry 11. The examination room 300 is a shield room which can shield a leakage magnetic field from the gantry 11 or an electromagnetic field from outside. In the examination room 300, a door D1 for entry/exit is provided. Between the examination room 300 and the control room 400, a door D2 for coming/going between the examination room 300 and the control room 400 is provided. In the control room 400, the console 27, the projector 100, and the projector control apparatus 200 are installed. The projector 100 is installed on the rear of the gantry 11 with a wall 500 between the examination room 300 and the control room 400 between them. A window 510 through which projection light LP can be transmitted is provided in a portion in the wall 500 to which the projection light LP from the projector 100 toward the movable screen unit 15 is propagated. Through the window 510, the projection light LP can be propagated from the projector 100 installed in the control room 400 to the movable screen unit 15 in the examination room 300. A door D3 for entry/exit is preferably provided in the control room 400.

The aforementioned layout is an example and is not limiting. For example, it was described that the projector 100, the projector control apparatus 200, and the console 27 are installed in the control room 400, but the console 27 and the projector control apparatus 200 may be installed in a room different from that for the projector 100. If the projector 100 can be formed of a material not susceptible to a magnetic field, the projector 100 may be provided in the examination room 300. Alternatively, a machine room or the like in which the gradient power supply 21 and the reception circuitry 25 are installed may be provided other than the examination room 300 and the control room 400.

Figure 4:
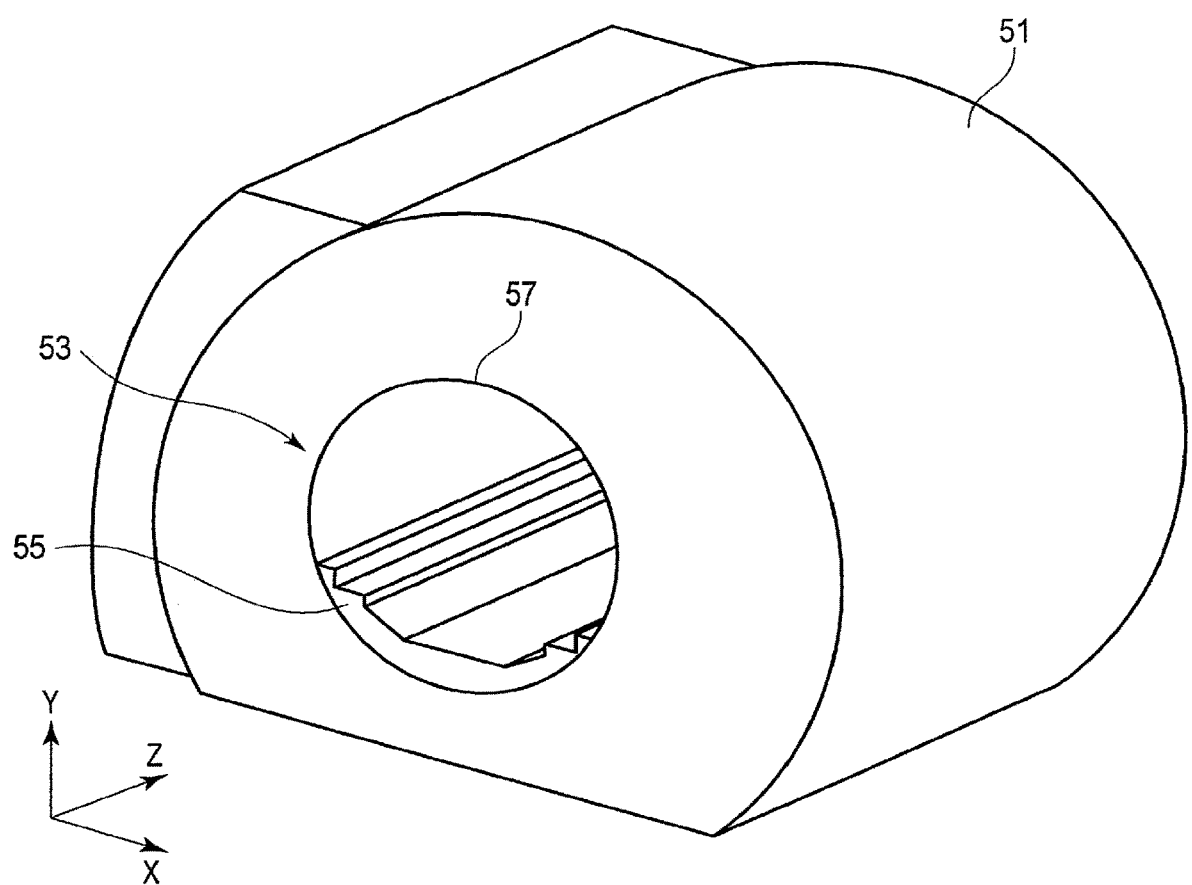
FIG. 4 is a perspective view of a gantry housing according to the embodiment.

Subsequently, an appearance of the gantry 11 will be described by referring to FIG. 4. FIG. 4 is a perspective view of the gantry housing 51 according to this embodiment. As illustrated in FIG. 4, the hollow bore 53 is formed in the gantry housing 51. On a lower part in the bore 53 of the gantry housing 51, a rail 55 in parallel with a center axis Z of the bore 53 is formed. The rail 55 is a construction guiding a slide along the center axis Z of the top plate 131 and the movable screen unit 15. The rail 55 is provided on an inner wall 57 of the gantry housing 51 in contact with the bore 53. The rail 55 is formed of a non-magnetic material not acting on a magnetic field used for magnetic resonance imaging. Here, a direction from couch side toward a projector side with respect to the Z-axis is specified as a +Z-axis direction, and a direction from the projector side toward the couch side is specified as a −Z-axis.

Subsequently, by referring to FIGS. 5, 6, 7, and 8, a structure of the movable screen unit 15 will be described. FIG. 5 is a perspective view of the movable screen unit 15 according to this embodiment. FIG. 6 is a side view of the movable screen unit 15. FIG. 7 is a front view of the movable screen unit 15. FIG. 8 is a perspective view of the movable screen unit 15 and the top plate 131 connected to each other.

As illustrated in FIGS. 5, 6, 7, and 8, the movable screen unit 15 has a movable truck 61, a screen 63, a support arm 65, and a reflecting plate 67. The movable truck 61 is a structural body moving along the rail 55 provided on the inner wall 57 of the gantry housing 51. On a lower part of the movable truck 61, a wheel (not shown) rolling on the rail 55 is mounted in order to improve running performance on the rail 55. If the movable truck 61 is capable of running on the rail 55, the wheel does not necessarily have to be provided but may be such that a surface in contact with the rail 55 is formed of a material having a low friction factor. The movable truck 61 and the rail 55 are formed such that the movable truck 61 is movable from an end portion on a couch 13 side (−Z side) of the bore 53 to an end portion on a projector 100 side (+Z side). A bottom surface of the movable truck 61 preferably has a shape capable of being fitted with the rail 55. By engaging the movable truck 61 with the rail 55, when the gantry 11 is seen from an outside in a state where the movable truck 61 is disposed on the end portion of the bore 53, the rail 55 can be made inconspicuous. The movable truck 61 supports the screen 63 and the support arm 65. The movable truck 61 is formed of a non-magnetic material such as a resin not acting on the magnetic field.

As illustrated in FIG. 5, a connection portion 69 to be connected to the top plate 131 is formed on the movable truck 61. By means of the connection portion 69, as illustrated in FIG. 8, the movable truck 61 and the top plate 131 are connected to each other. A patient fixture 137 is mounted on a front part (+Z-axis direction side) of the top plate 131. The patient fixture 137 fixes a head part of the patient P placed on the top plate 131. The patient fixture 137 has a curved shape so that it can cover a rear head part without shielding a visual field of the patient P placed on the top plate 131. That is, a front head part side of the patient fixture 137 is open. Thus, the patient fixture 137 can alleviate a locked up feeling of the patient P as compared with a fixing portion covering the entire head part and can alleviate narrowing of the visual field of the patient P. The patient fixture 137 is integrally molded by a non-magnetic material such as a resin by using a die having the aforementioned shape, for example.

As illustrated in FIGS. 5, 6, 7, and 8, the screen 63 is installed upright on the movable truck 61. On the screen 63, a image from the projector 100, not shown, is projected. The screen 63 is provided capable of being tilted with respect to the movable truck 61. Specifically, it is provided capable of being tilted by a tilting mechanism (not shown) provided on the movable truck 61. By adjusting a tilting angle of the screen 63 with respect to a surface of the movable truck 61, the screen 63 is held vertically or at a predetermined tilting angle to the surface of the movable truck 61. As described above, the projector 100 is disposed on a side opposite to the couch 13 with the screen 63 between them. Here, it is assumed that a surface of the screen 63 on the projector 100 side is called a back surface and a surface on the couch 13 side as a front surface. In order to project the image on the front, the screen 63 is preferably formed of a translucent material. As such translucent material, translucent plastic or frosted glass is preferably used. By forming the screen 63 of the translucent material, projection light ejected from the projector 100 is irradiated to the back surface of the screen, and the image corresponding to the projection light is projected on the front surface. As a result, the patient P or the like can see the image projected on the front surface from the couch 13 side. The screen 63 may be of a type having a planar shape or of a type having a curved surface. If it has the curved shape, a recess surface is preferably directed to the couch 13 side, that is, the recess surface forms a front surface. By directing the recess surface to the couch 13 side, a periphery of the rear of the head part of the patient P placed on the top plate 131 can be covered by the screen 63. As a result, the visual field of the patient P can be filled with the image projected on the screen 63 so that the patient can be immersed in the image.

Figure 9:
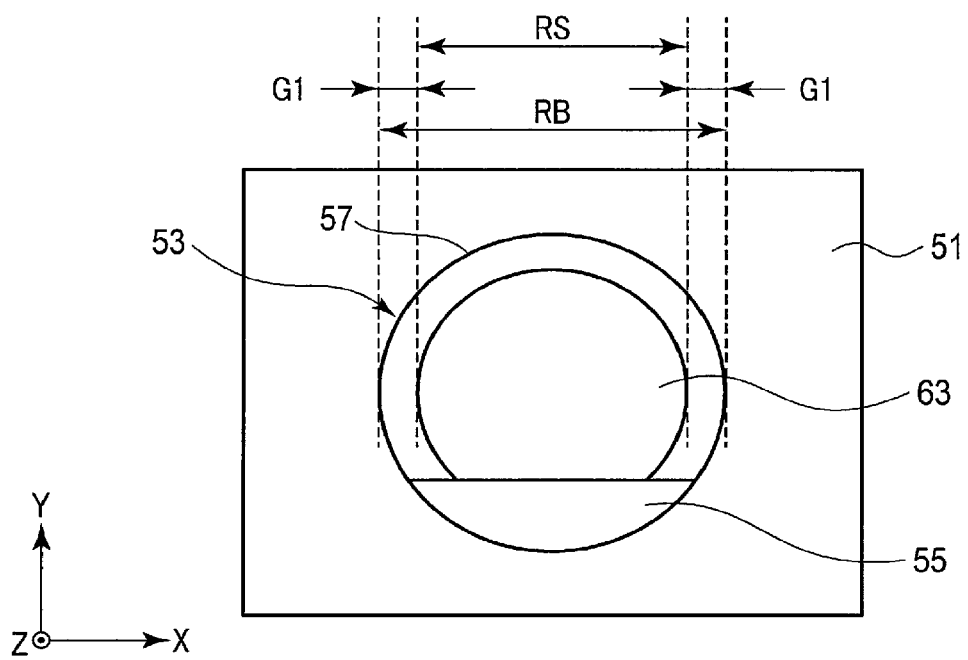
FIG. 9 is a diagram according to the embodiment and illustrating a front of a screen disposed in a bore.

FIG. 9 is a schematic front view of the screen 63 disposed in the bore 53. As illustrated in FIG. 9, the screen 63 has an outer diameter RS smaller than a diameter RB of the inner wall 57 in contact with the bore 53 of the gantry housing 51. By designing the outer diameter RS smaller than the inner diameter RB as above, the movable screen unit 15 can be inserted into the bore 53. Air is flowing through the bore 53 from a ventilation fan (not shown) provided on the gantry 11. By providing a gap G1 between an edge of the screen 63 and the inner wall 57, the air sent out of the ventilation fan can be prevented from being shut off by the screen 63. The outer diameter RS is preferably designed smaller than the inner diameter RB by 10 mm to 50 mm. In other words, the gap G1 is preferably designed to 10 mm to 50 mm.

As illustrated in FIGS. 5, 6, 7, and 8, the support arm 65 is mounted on the movable truck 61. As will be described later, the support arm 65 is mounted on the movable truck 61 slidably with respect to the Z-axis direction. The support arm 65 supports the reflecting plate 67 to arrange the reflecting plate 67 in a space on the front surface side of the screen 63. The reflecting plate 67 is supported by the support arm 65 away from the surface of the movable truck 61 to such a degree that it does not hit the head part of the patient P placed on the top plate 131 in a state where the movable truck 61 and the top plate 131 are connected. The support arm 65 has a shape that does not shield the visual field of an outside observer when the screen 63 is seen from outside of the gantry 11. In order not to shield the visual field of the outside observer, the support arm 65 preferably has a semi-annular shape or a semi-saddle shape having an arc portion along a profile of the screen 63 as illustrated in FIGS. 5, 6, 7, and 8. In this case, both ends of the support arm 65 are mounted on side parts of the movable truck 61, and the support arm 65 is mounted on the movable truck 61 so that the arc portion of the support arm 65 is located in the space on the front surface side of the screen 63. A shape of the support arm 65 is not limited to the aforementioned semi-annular shape or semi-saddle shape but may have any shape as long as the reflecting plate 67 can be disposed in the space on the front surface side of the screen 63. For example, the support arm 65 may be constituted by a pair of arms each having a substantially rod shape. In this case, one ends of the pair of arms are preferably mounted on both side parts of the movable truck 61, while the reflecting plate 67 on the other ends.

As illustrated in FIGS. 5, 6, 7, and 8, the reflecting plate 67 is provided on a substantially uppermost part of the support arm 65. The reflecting plate 67 reflects the image projected on the front surface of the screen 63. The reflecting plate 67 is formed of a non-magnetic material and may be formed by any material as long as it can optically reflect a target. For example, as the reflecting plate 67, a mirror in which aluminum deposition processing is applied to acryl or a half mirror to which a dielectric film is deposited may be preferably used. The patient P with the head part disposed on the patient fixture 137 can see the image projected on the front surface through the reflecting plate 67.

The reflecting plate 67 is rotatably provided on the support arm 65 in order to manually adjust an angle of the reflecting plate 67 by the patient P. Specifically, it is provided rotatably around a rotating shaft RR1 by a rotating mechanism (not shown) provided on the support arm 65. The rotating shaft RR1 is provided in parallel with an X-axis so that a direction of the reflecting plate 67 can be adjusted with respect to the front surface of the screen 63, for example. In more detail, the support arm 65 is preferably provided switchably between a first angle for a first projection mode and a second angle for a second projection mode which will be described later. The first projection mode is a format of seeing an image on the screen 63 outside the gantry 11 not through the reflecting plate 67. Thus, the first angle of the reflecting plate 67 in the first projection mode is preferably set to an angle not shielding the visual field of the patient P or the like outside the gantry 11 or substantially horizontally, for example. The second projection mode is a format of seeing the image through the reflecting plate 67 inside the bore 53. Thus, the second angle of the reflecting plate in the second projection mode is preferably set to an arbitrary angle between horizontal and vertical in accordance with a body build or the like of the patient P who is an observer.

Figure 10:
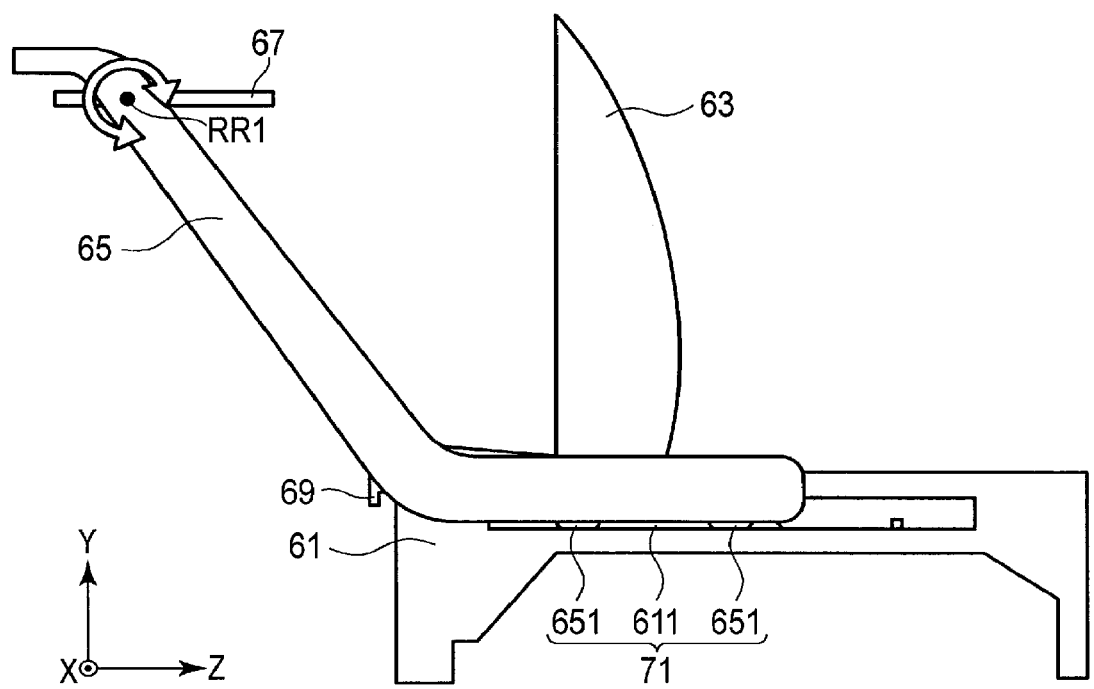
FIG. 10 is a view according to the embodiment and illustrating a side surface of the movable screen unit on which a slide mechanism is mounted.

In order to adjust a position of the reflecting plate 67 with respect to the Z-axis, a slide mechanism 71 of the support arm 65 is preferably provided on the movable truck 61. FIG. 10 is a view illustrating a side surface of the movable screen unit 15 in which the support arm 65 in FIG. 6 is slide with respect to the Z-axis. As illustrated in FIGS. 6 and 10, the slide mechanism 71 has a guide 611 for guiding a slide along the Z-axis of the support arm 65 formed on the movable truck 61. The guide 611 is provided along the Z-axis on both side surfaces of the movable truck 61 in order to avoid contact with the support arm 65 and the screen 63. The guide 611 may be realized in any mode but it is realized by a gap provided along the Z-axis on the side surface of the movable truck 61, for example. As illustrated in FIGS. 6 and 10, in order to improve sliding performance of the support arm 65, a wheel 651 is preferably provided on a base portion faced with the guide 611 in the support arm 65. By providing the slide mechanism 71, the reflecting plate 67 can be brought closer to or separated from the screen 63 by pushing or pulling of the support arm 65 in the Z-axis direction by a medical staff such as doctor, a technician, and a nurse and the patient P or the like. As a result, the position of the reflecting plate 67 with respect to the Z-axis direction can be adjusted.

In the aforementioned explanation, the slide mechanism 71 is realized by the guide 611 provided on the movable truck 61 and the wheel 651 provided on the support arm 65. However, this embodiment is not limited to that. As the slide mechanism 71 according to this embodiment, any mechanism may be used as long as it can relatively slide the support arm 65 with respect to the movable truck 61. For example, a guide along the Z-axis may be provided on the support arm 65 and a wheel running on the guide may be provided on the movable truck 61. Moreover, the slide mechanism 71 may be realized by a ball screw, a slide rail or the like.

Figure 11:
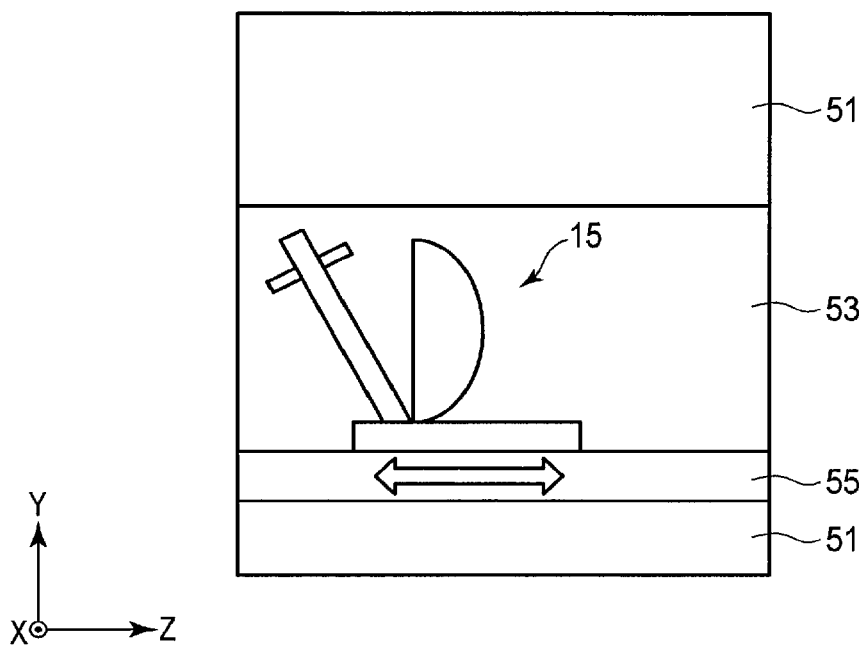
FIG. 11 is another diagram according to the embodiment illustrating a side surface of the movable screen unit on which a slide mechanism is mounted.

FIG. 11 is a simple side view of the movable screen unit 15 disposed in the bore 53 of the gantry 11. As illustrated in FIG. 11, the movable truck 61 of the movable screen unit 15 is slidably provided on the rail 55. Typically, the movable screen unit 15 does not have a driving device mounted. The movable screen unit 15 slides in conjunction with sliding of the top plate 131 by the couch actuator 135. The movable screen unit 15 can slide with respect to the Z-axis by pushing or puling by the patient P or the medical staff.

By means of the aforementioned configuration, the medical image diagnosis apparatus 10 according to this embodiment can realize the first projection mode of projecting an image on the movable screen unit 15 in a state where the movable screen unit 15 is disposed on the end portion on the couch side of the bore 53 and the second projection mode of projecting an image on the movable screen unit 15 in a state where the top plate 131 and the movable screen unit 15 are connected.

FIG. 12 is a view illustrating the movable screen unit 15 in the first projection mode from a side of the gantry 11. FIG. 13 is a view illustrating the movable screen unit 15 in the first projection mode from a front of the gantry 11. As illustrated in FIGS. 12 and 13, in the first projection mode, the movable screen unit 15 is disposed so that the screen 63 is located on the end portion on the couch side of the bore 53. In the first projection mode, the patient P or the medical staff sees an image PI projected on the screen 63 from an outside of the gantry housing 51 not through the reflecting plate 67. Since the screen 63 is disposed on the end portion on the couch side, the screen 63 blocks the bore 53, and the patient P is prevented from seeing an inside of the bore 53. Moreover, since the image PI is projected on the screen 63, recognition of the patient P that the bore 53 is an imaging space is dulled and a fear caused by entry into the bore 53 can be alleviated. Hereinafter, a geometry of the gantry 11, the couch 13, and the movable screen unit 15 for the first projection mode shall be called a first case.

FIG. 14 is a view illustrating the movable screen unit 15 in the second projection mode from the side of the gantry 11. As illustrated in FIG. 14, in the second projection mode, the patient P sees the image projected on the surface of the screen 63 through the reflecting plate 67 in a state placed on the top plate 131 and inserted into the bore 53. Since the top plate 131 and the movable screen unit 15 are connected, a distance between the patient P and the screen 63 is kept constant regardless of the slide of the movable screen unit 15 in the Z-axis direction. Thus, a feeling of being immersed in the image projected on the screen 63 is deepened, and the locked up feeling in the bore 53 can be alleviated. Hereinafter, a geometry of the gantry 11, the couch 13, and the movable screen unit 15 for the second projection mode shall be called a second case.

The position signal output from the position detector 19 is an electric signal relating to the position of the couch 13 and the movable screen unit 15 and thus, a data value changes in accordance with switching between the first case and the second case. In other words, the positions of the couch 13 and the movable screen unit 15 function as indexes for discriminating between the first case and the second case.

As described above, in the first projection mode, the patient P visually recognizes the image projected on the screen 63 directly not through the reflecting plate 67, while in the second projection mode, the patient P visually recognizes the image projected on the screen 63 through the reflecting plate 67. Thus, when switching is made between the first projection mode and the second projection mode, from the patient P's point of view, the image looks reversed, and the patient P feels discomfort.

The projector control apparatus 200 according to this embodiment controls the projector 100 so that the patient does not feel discomfort even if switching is made between the first projection mode and the second projection mode.

Figure 15:
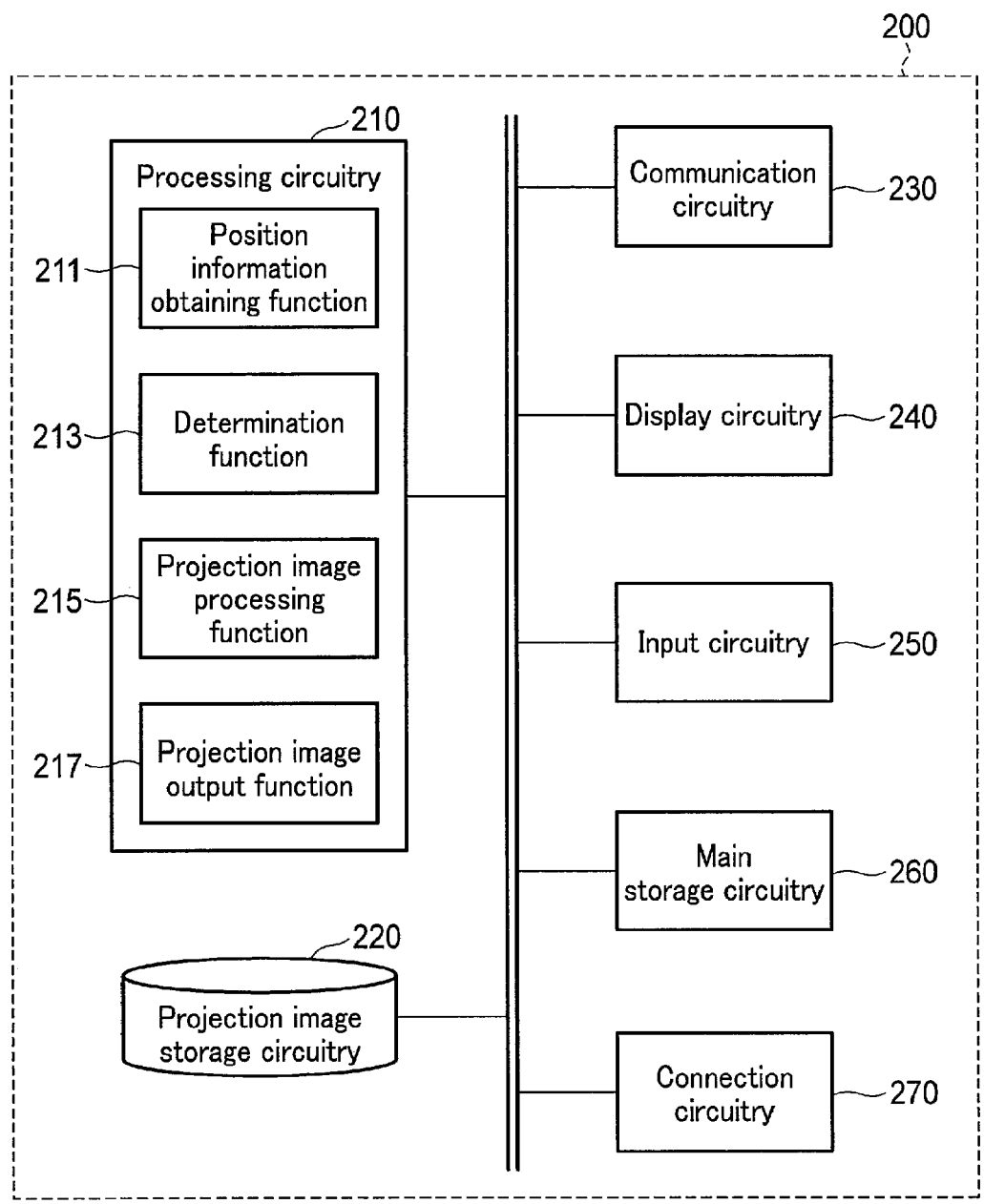
FIG. 15 is a diagram illustrating configuration of a projector control apparatus according to the embodiment.

FIG. 15 is a view illustrating configuration of the projector control apparatus 200 according to this embodiment. As illustrated in FIG. 15, the projector control apparatus 200 according to this embodiment has a processing circuitry 210, a projection image storage circuitry 220, a communication circuitry 230, a display circuit 240, an input circuit 250, a main storage circuitry 260, and a connection circuitry 270. The processing circuitry 210, the projection image storage circuitry 220, the communication circuitry 230, the display circuitry 240, the input circuitry 250, the main storage circuitry 260, and the connection circuitry 270 are communicably connected to each other through a bus.

The projection image storage circuitry 220 stores image data relating to the image projected on the movable screen unit 15. The projection image may be a still image constituted by one frame or may be a moving image constituted by a plurality of frames arrayed in a time series. In order to make explanation below specific, the projection image is assumed to be a moving image. Hereinafter, the projection image is referred to as video. For example, image data of a plurality of frames constituting one video is stored as one file in the projection image storage circuitry 220. In this embodiment, the projection image storage circuitry 220 stores the image data relating to the video projected on the movable screen unit 15 in the first projection mode (hereinafter referred to as first video) and the image data relating to the video projected on the movable screen unit 15 in the second projection mode (hereinafter referred to as second video) as individual files.

The communication circuitry 230 conducts data communication with the console 27 or other computers via a wire, not shown, or wirelessly. For example, the communication circuitry 230 receives the image data relating to the video from the other computers. The image data relating to the received video is stored in the projection image storage circuitry 220.

The display circuitry 240 displays various types of information. For example, the display circuitry 240 displays the video corresponding to the video signal supplied to the projector 100 on a real time basis. Specifically, the display circuitry 240 has a display interface circuit and a display device. The display interface circuit converts the video data relating to the video to be displayed to a video signal. The video signal is supplied to the display device. The display device displays the video signal to be displayed. As the display device, for example, a CRT display, a liquid crystal display, an organic EL display, an LED display, a plasma display or other arbitrary displays known in this technical field can be used as appropriate.

The input circuitry 250 specifically has an input device and an input interface circuit. The input device receives various instructions from the user. As the input device, a keyboard, a mouse, various switches and the like can be used. The input interface circuit supplies an output signal from the input device to the processing circuitry 210 through the bus.

The main storage circuitry 260 is a storage device such as an HDD (hard disk drive), an SSD (solid state drive), and an integrated circuit storage device storing various types of information. The main storage circuitry 260 may be a CD-ROM drive, a DVD drive, and a driving device for reading/writing various types of information with portable storage medium such as a flash memory. For example, the main storage circuitry 260 stores a video projection program and the like according to this embodiment.

The connection circuitry 270 is an interface circuit for supplying a video signal to the projector 100 through via a wire, not shown, or wirelessly. The connection circuitry 270 may supply an analog video signal in accordance with the projection format of the projector 100 or may supply a digital video signal. Hereinafter the video signal supplied to the projector 100 according to this embodiment is not discriminated into the analog video signal and the digital video signal but simply referred to as the video signal.

The processing circuitry 210 has a processor such as a CPU, a GPU, and an MPU and a memory such as a ROM and a RAM as hardware resources. The processing circuitry 210 functions as a center of the projector control apparatus 200. The processing circuitry 210 reads out the image projection program stored in the main storage circuitry 260, expand it on the memory, and execute the expanded image projection program. By executing the image projection program, the processing circuitry 210 realizes a position information obtaining function 211, a determination function 213, a projection image processing function 215, and a projection image output function 217.

By executing the position information obtaining function 211, the processing circuitry 210 obtains a position signal supplied from the position detector 19 directly or through the console 27 indirectly.

By executing the determination function 213, the processing circuitry 210 determines whether switching from the first case to the second case has been made based on the position signal obtained by the position information obtaining function 211. In other words, the processing circuitry 210 determines whether couch 13 or the movable screen unit 15 is in the first case or in the second case.

By executing the projection image processing function 215, the processing circuitry 210 applies various processing such as image processing, playback processing and the like to the image data relating to image to be projected. As the image processing, the processing circuitry 210 executes mirror image inversion processing or arbitrary angle rotation processing, for example. Specifically, the processing circuitry 210 inverts the image data relating to the video right and left or up and down in the mirror image inversion processing. In the arbitrary angle rotation processing, the processing circuitry 210 rotates the image data relating to the video around its center point only by a predetermined angle. It is assumed that the right-and-left inversion refers to inversion with respect to the X-axis direction and the up-and-down inversion refers to inversion with respect to the Y-axis direction. As the image processing, the processing circuitry 210 may execute arbitrary image processing such as color inversion processing, enlargement/reduction processing, and clipping processing. As playback processing, the processing circuitry 210 executes frame search processing and the like. Specifically, the processing circuitry 210 specifies a frame where playback is started in a plurality of frames constituting the image data relating to the video. As the playback processing, the processing circuit may execute playback speed changing processing, playback direction changing processing and the like.

By execution of the projection image output function 217, when the processing circuitry 210 determines that switching to the second case has not been made by the determination function 213, the processing circuitry 210 outputs the first video signal to the projector 100. While when processing circuitry 210 determines that switching to the second case has been made by the determination function 213, processing circuitry 210 outputs the second video signal to the projector 100. The first video signal is a video signal relating to the video projected on the movable screen unit 15 in the first projection mode (hereinafter referred to as the first video). The second video signal is a video signal relating to the video projected on the movable screen unit 15 in the second projection mode (hereinafter referred to as the second video). The first video and the second video may have the same contents or different contents. In this embodiment, the contents means substantive information (contents) of the video. For example, since original video and secondary video generated by applying the image processing to the original video share the substantive information, they are assumed to have the same contents. Moreover, in each of the first video and the second video, if the same subject is projected, and even if the subject is projected so that it is made to look different between the first video and the second video by the image processing, the first video and the second video are assumed to have the same contents.

Figure 16:
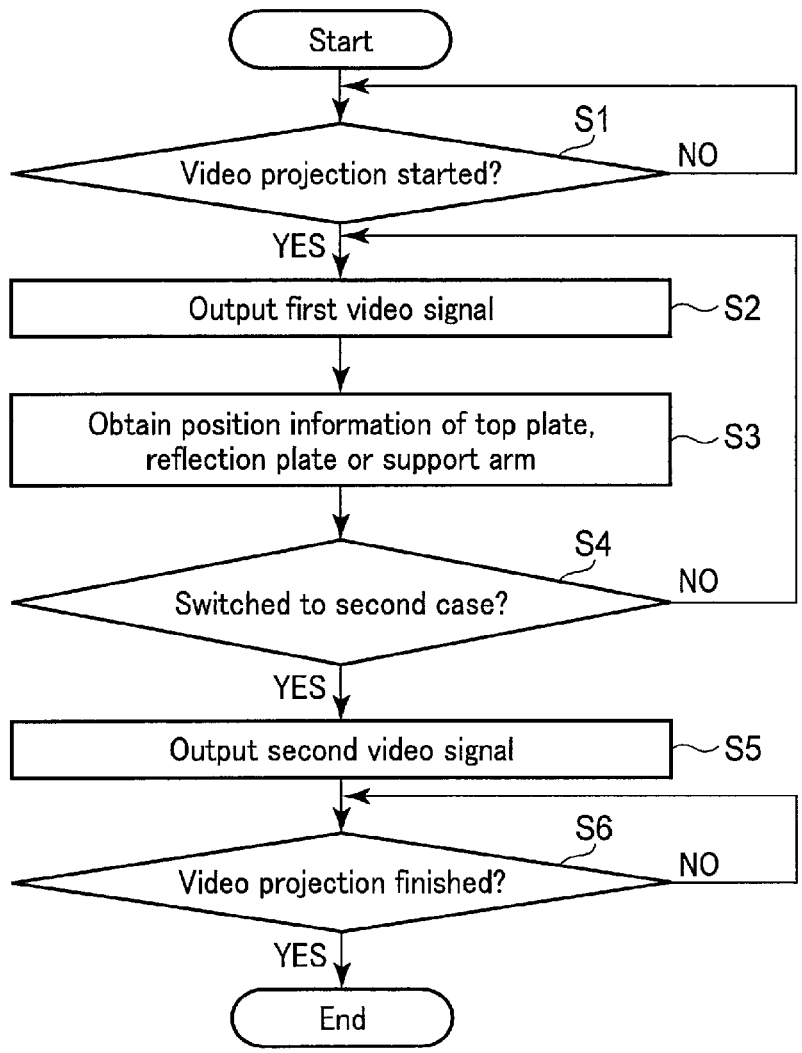
FIG. 16 is a diagram illustrating a typical flow of image projection processing executed by a processing circuitry in accordance with an image projecting program according to the embodiment.

Subsequently, image projection processing executed by the processing circuitry 210 in accordance with an image projection program according to this embodiment will be described. FIG. 16 is a diagram illustrating a typical flow of the image projection processing executed by the processing circuitry 210 in accordance with the image projecting program according to the embodiment. The image projection program is read out from the main storage circuitry 37 and executed by the processing circuitry 210 upon receipt of a start instruction by the medical staff or the like through the input circuitry 250. The position detector 19 is assumed to repeatedly detect a position of a specific construction included in the couch 13 or the movable screen unit 15 from before start of the image projection processing. In the explanation below of the image projection processing, the construction of the position detection target is assumed to be the top plate 131, the reflecting plate 67 or the support arm 65.

First, the processing circuitry 210 waits for the start instruction of projection of the first video (Step S1). The projection of the first video can be started at any timing if the movable screen unit 15 is disposed on the end portion on the couch side of the bore 53. However, for the purpose not to make the patient P sense the bore 53, it is preferably started before the patient P enters the examination room 300. Projection start is received by the processing circuitry 210 upon receipt of the start instruction by the medical staff or the like through the input circuitry 250, for example.

When the start instruction of projection of the first video is given, the processing circuitry 210 executes the projection image output function 217 (Step S2). At Step S2, the processing circuitry 210 outputs the first video signal to the projector 100 through the connection circuitry 270. Specifically, the processing circuitry 210 first reads out the image data of the first image from the projection image storage circuitry 220. Then, the processing circuitry 210 coverts the image data of the read-out first video to the first video signal by the unit of frame and outputs it to the projector 100 through the first connection circuitry 270 by the unit of frame in a time series. The projector 100 having received the first video signal projects the first video signal to the movable screen unit 15. As a result, the patient P or the medical staff outside the gantry 11 can see the video projected on the screen 63 of the movable screen unit 15.

When Step S2 is executed, the processing circuitry 210 executes the position information obtaining function 211 (Step S3). At step S3, the processing circuitry 210 obtains the position signals of the top plate 131, the reflecting plate 67 or the support arm 65 transmitted from the position detector 19.

When Step S3 is executed, the processing circuitry 210 executes the determination function 213 (Step S4). At Step S4, the processing circuitry 210 determines whether or not the top plate 131, the reflecting plate 67 or the support arm 65 has switched from the first case to the second case based on the position signal of the top plate 131, the reflecting plate 67 or the support arm 65. If it is determined that the top plate 131, the reflecting plate 67 or the support arm 65 has not been switched to the second case (Step S4: NO), the processing circuitry 210 estimates that the top plate 131, the reflecting plate 67 or the support arm 65 is still in the first case. Then, the processing circuitry 210 repeats Steps S2, S3, and S4 until switching to the second case. Here, switching between the first case and the second case of each of the top plate 131, the reflecting plate 67, and the support arm 65 will be described.

Figure 17:
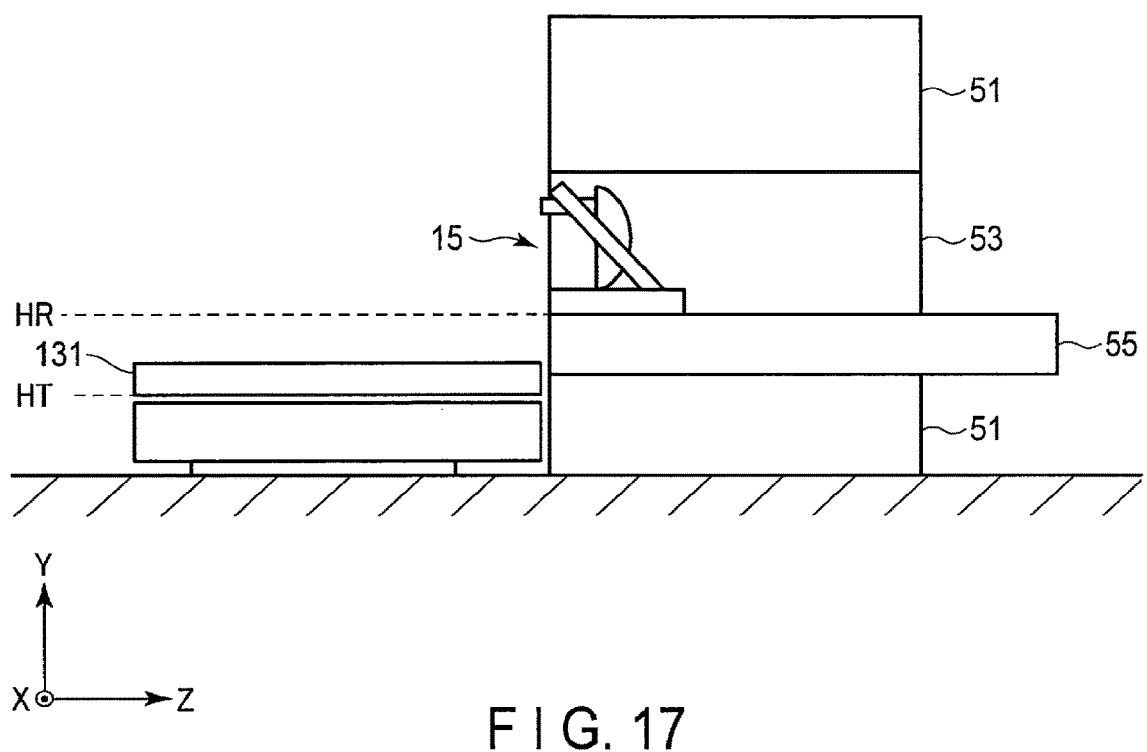
FIG. 17 is a view illustrating the top plate in a first case according to the embodiment.
Figure 18:
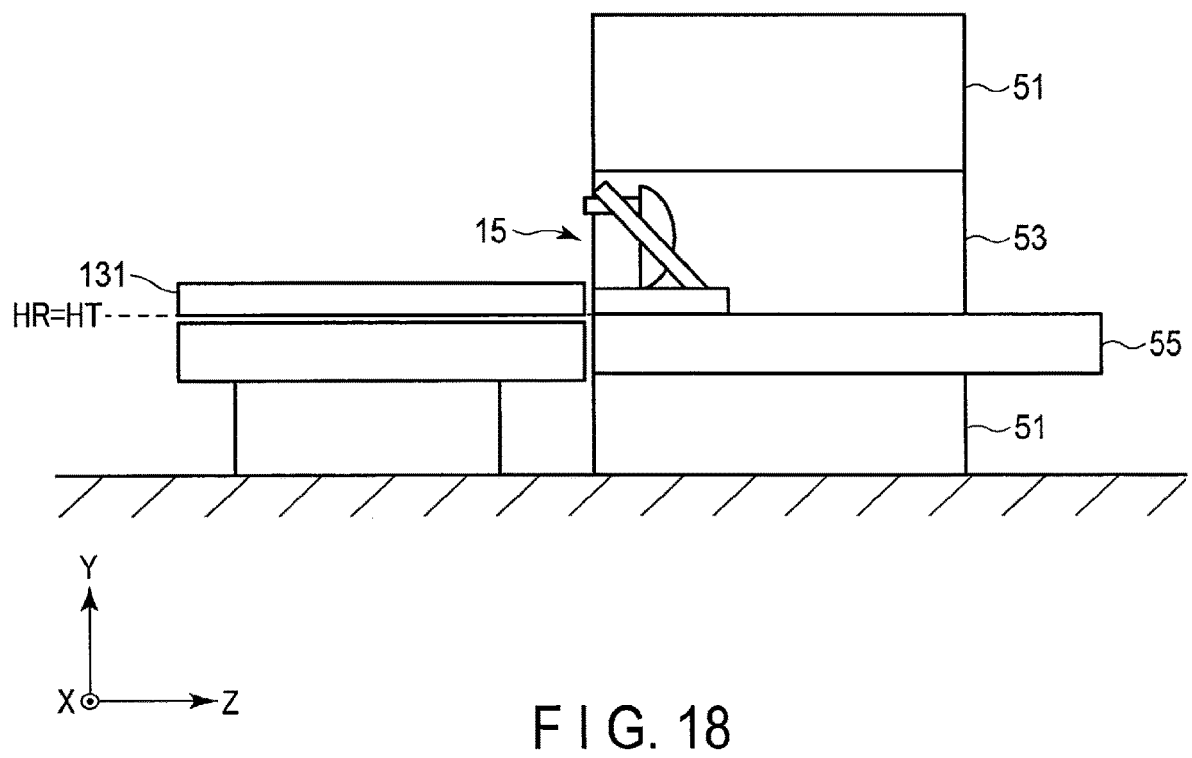
FIG. 18 is a view illustrating the top plate in a second case according to the embodiment.

FIG. 17 is a view illustrating the top plate 131 in the first case. FIG. 18 is a view illustrating the top plate 131 in a second case. As illustrated in FIG. 17, since the first case is where the patient or the like to see the video projected on the movable screen unit 15 from the outside of the gantry 11, the patient is not placed on the top plate 131, and a height HT of the top plate 131 is lower than a height (hereinafter referred to as an insertable height) HR which can be inserted into the bore 53. As illustrated in FIG. 18, since the second case is where the patient placed on the top plate 131 in the bore 53 to see the video projected on the movable screen unit 15 through the reflecting plate 67, the height HT of the top plate 131 is the same as or higher than the insertable height HR. Thus, a reference value for discriminating whether the top plate 131 is in the first case or in the second case is preferably set to the insertable height HR. As the position detector 19 of the height HT of the top plate 131, a position sensor such as an optical or ultrasonic, a rotary encoder mounted on a motor for elevating the top plate 131 or an optical camera for photographing the top plate 131 is appropriate.

At Step S4, the processing circuitry 210 repeatedly measure the height HT of the top plate 131 based on the position signal from the position detector 19. The processing circuitry 210 compares the height HT of the top plate 131 with the insertable height HR at predetermined time intervals. And if the height HT is lower than the height HR, the processing circuitry 210 determines that the top plate 131 is in the first case, that is, the switching from the first case to the second case has not been made. While if the height HT is higher than or equal to the height HR, the processing circuitry 210 determines that the top plate 131 is in the second case, that is, the switching from the first case to the second case has been made.

In the aforementioned determination method, whether or not the height HT of the top plate 131 matches the insertable height HR is determined at predetermined time intervals. However, this embodiment is not limited to that. For example, in the case that the height HT matches the insertable height HR, that is, the switching from the first case to the second case may be detected by the position detector 19. In this case, the position detector 19 may be an optical sensor constituted by combination of a light source and a photodetector. For example, the light source may be provided on the end portion of the top plate 131 on the gantry side and the photodetector may be provided on the end portion of the movable truck 61 on the couch side. When the end portion of the top plate 131 on the gantry side gets closer to the end portion of the movable truck 61 on the couch side, the optical sensor outputs an ON signal, while it is separated away, the optical sensor outputs an OFF signal. That is, the processing circuitry 210 can determine that the top plate 131 is in the first case when the ON signal is output, and that the top plate 131 is in the second case when the OFF signal is output. In other words, when output is switched from the ON signal to the OFF signal, the processing circuitry 210 determines that the switching from the first case to the second case has been made. By means of this configuration, the first image can be switched to the second image using arrival of the top plate 131 at the insertable height HR as a trigger. The arrangement of the light source and the photodetector is not limited only to the above but may be switched.

Figure 19:
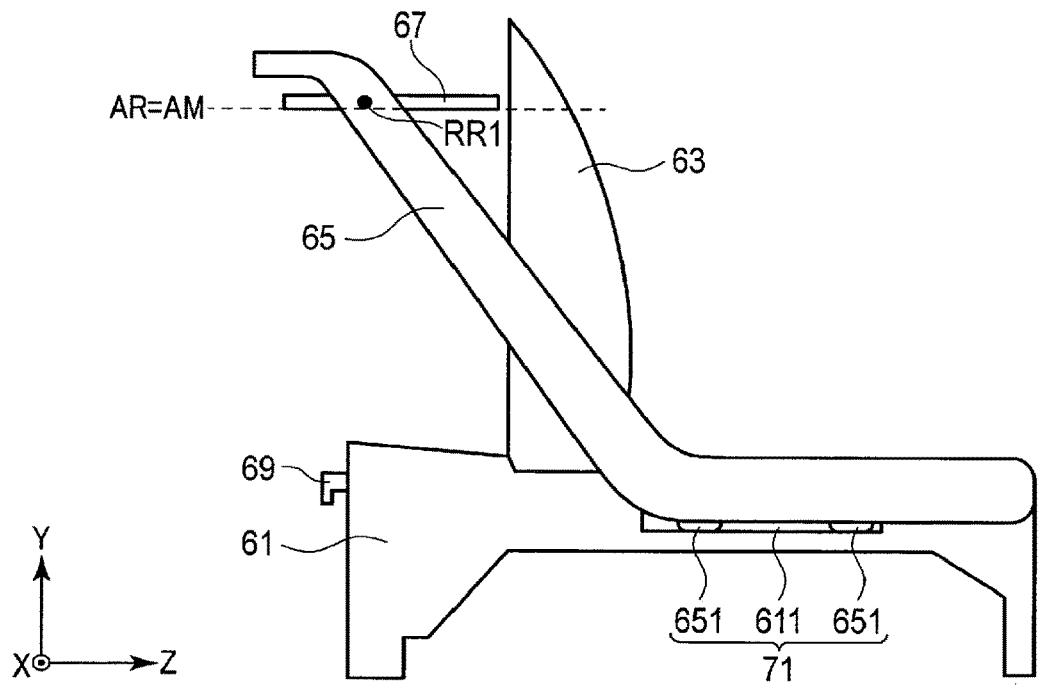
FIG. 19 is a view illustrating a reflecting plate in a first case according to the embodiment.
Figure 20:
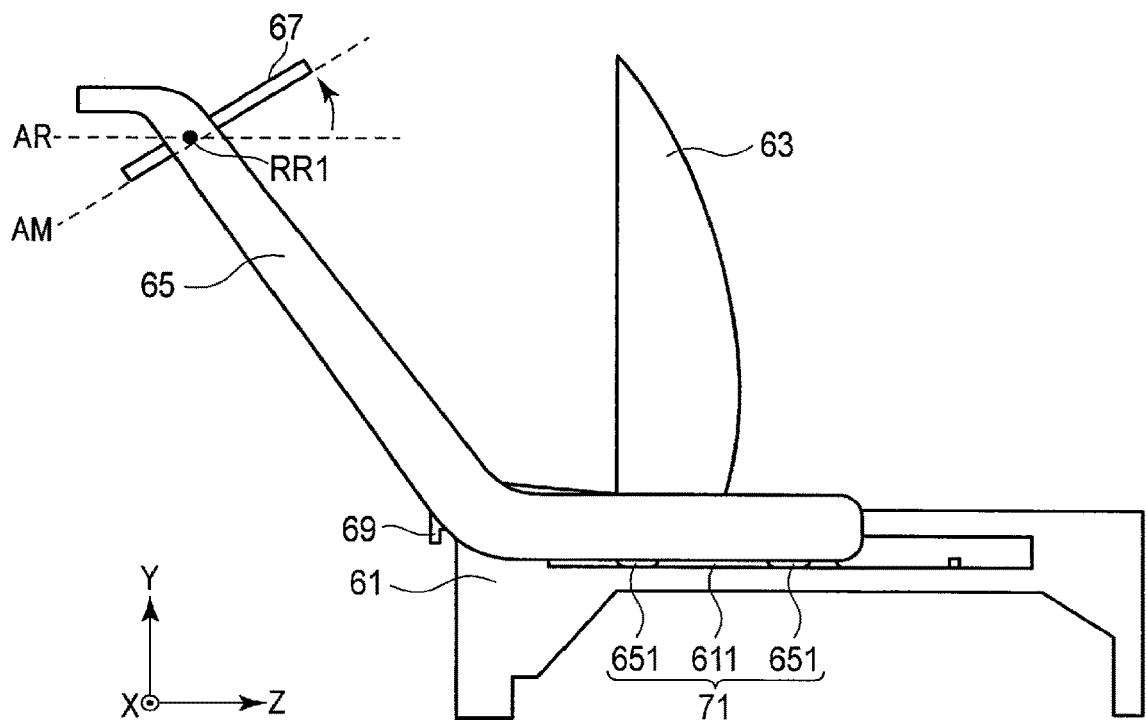
FIG. 20 is a view illustrating the reflecting plate in a second case according to the embodiment.

FIG. 19 is a view illustrating the reflecting plate 67 in the first case. FIG. 20 is a view illustrating the reflecting plate 67 in the second case. As illustrated in FIG. 19, since the first case is a mode for the patient or the like to see the video projected on the movable screen unit 15 from the outside of the gantry 11, a rotation angle AM around the rotating shaft RR1 of the reflecting plate 67 is held substantially horizontally by the support arm 65. This rotation angle of the reflecting plate 67 around the rotating shaft RR1 corresponding to substantially horizontal shall be referred to as a substantially horizontal angle AR. As illustrated in FIG. 20, since the second case is where the patient placed on the top plate 131 in the bore 53 to see the video projected on the movable screen unit 15 through the reflecting plate 67, the rotation angle AM of the reflecting plate 67 is inclined from the substantially horizontal angle AR. Thus, a reference value for discriminating whether the reflecting plate 67 is in the first case or in the second case may be set to the substantially horizontal angle AR. As the position detector 19 for detecting the rotation angle AM of the reflecting plate 67, a rotary encoder or the like mounted on the rotating shaft RR1 is appropriate.

At Step S4, the processing circuitry 210 repeatedly measures the rotation angle AM of the reflecting plate 67 based on the position signal from the position detector 19. Then, the processing circuitry 210 compares the rotation angle AM of the reflecting plate 67 with the substantially horizontal angle AR at the predetermined time intervals. And if the rotation angle AM matches the substantially horizontal angle AR, processing circuitry 210 determines that the reflecting plate 67 is in the first case, that is, the switching from the first case to the second case has not been made. While if the rotation angle AM does not match the substantially horizontal angle AR, processing circuitry 210 determines that the reflecting plate 67 is in the second case, that is, the switching from the first case to the second case has been made.

In the aforementioned determination method, whether or not the rotation angle AM of the reflecting plate 67 matches the substantially horizontal angle AR is determined at the predetermined time intervals. However, this embodiment is not limited to that. For example, a shift of the rotation angle AM from the substantially horizontal angle AR, that is, the switching from the first case to the second case may be detected by the position detector 19. In this case, the position detector 19 may be a rotary encoder or the like mounted on the rotating shaft RR1. The rotary encoder outputs a pulse signal (position signal) at every rotation of the reflecting plate 67 at a predetermined angle around the rotating shaft RR1. That is, the processing circuitry 210 can determine that the reflecting plate 67 is in the first case from start of the video projection processing to the output of the pulse signal. And by using the output of the pulse signal as a trigger, processing circuitry 210 can determine that the reflecting plate 67 has been switched from the first case to the second case. By means of this configuration, the first video is switched to the second video triggered that the patient P is placed on the top plate 131 and the reflecting plate 67 is rotated around the RR1 shaft in order to adjust the angle of the reflecting plate 67.

Figure 21:
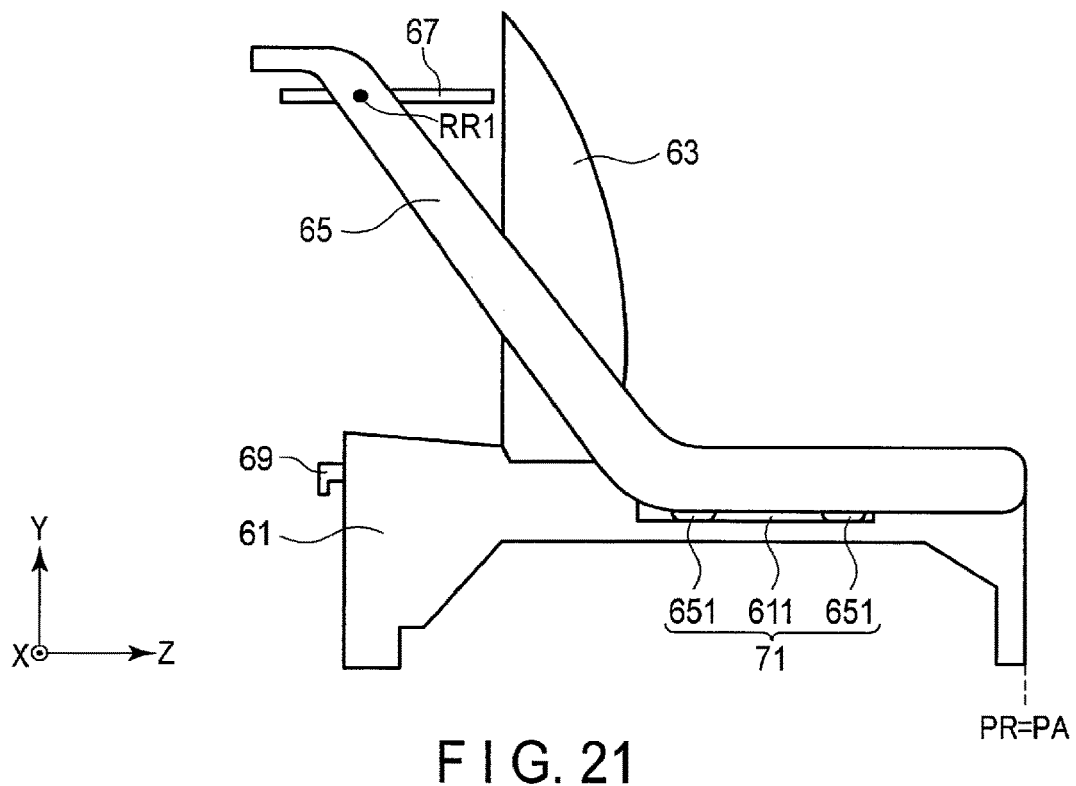
FIG. 21 is a view illustrating a support arm in a first case according to the embodiment.
Figure 22:
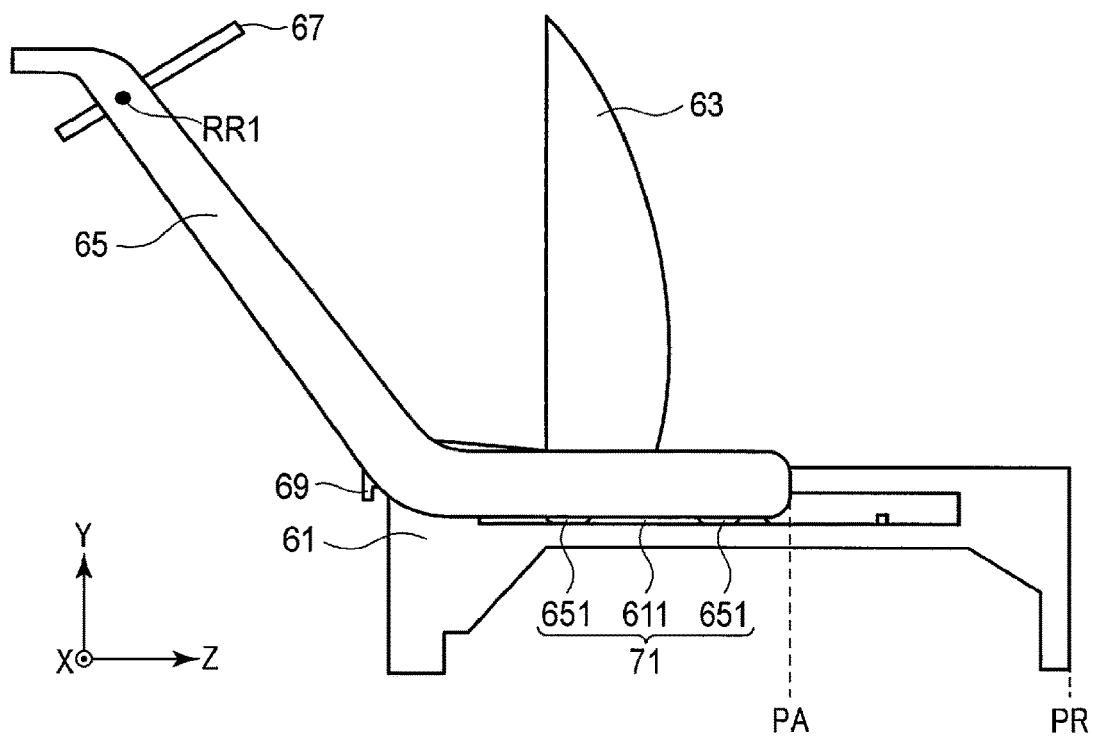
FIG. 22 is a view illustrating the support arm in a second case according to the embodiment.

FIG. 21 is a view illustrating the support arm 65 in the first case. FIG. 22 is a view illustrating the support arm 65 in the second case. As illustrated in FIG. 21, since the first case is a mode for the patient or the like to see the video projected on the movable screen unit 15 from the outside of the gantry 11, the support arm 65 is stored in the movable truck 61. A position PA of a characteristic point in the Z-axis direction of the support arm 65 when the support arm 65 is stored in the movable truck 61 shall be referred to as a storage position PR. The characteristic point may be any portion in the support arm 65 but as illustrated in FIGS. 21 and 22, it is assumed to be an end portion of the support arm 65. As illustrated in FIG. 22, since the second case is where the patient placed on the top plate 131 in the bore 53 to see the video projected on the movable screen unit 15 through the reflecting plate 67, the position PA of the support arm 65 in the Z-axis direction is withdrawn from the storage position PR toward the couch side. Thus, it can be determined that, if the position PA of the support arm 65 is located at the storage position PR, the support arm 65 is in the first arrangement for, while if the position PA of the support arm 65 is not located at the storage position PR, the support arm 65 is in the second case. Thus, a reference value for discriminating whether the support arm 65 is in the first case or in the second case may be set to the storage position PR. As the position detector 19 for detecting the position PA of the characteristic point of the support arm 65, a position sensor or the like mounted on the characteristic point is appropriate.

At Step S4, the processing circuitry 210 repeatedly measure the position PA of the support arm 65 based on the position signal from the position detector 19. Then, the processing circuitry 210 compares the position PA of the support arm 65 with the storage position PR at the predetermined time intervals. And the processing circuitry 210 determines that, if the position PA matches the storage position PR, the support arm 65 is in the first case, that is, the switching from the first case to the second case has not been made. While if the position PA does not match the storage position PR, the processing circuitry 210 determines that the support arm 65 is in the second case, that is, the switching from the first case to the second case has been made.

In the aforementioned determination method, whether or not the position PA of the support arm 65 matches the storage position PR is determined at the predetermined time intervals. However, this embodiment is not limited to that. For example, a shift of the position PA from the storage position PR may be detected by the position detector 19. In this case, the position detector 19 can be realized by an optical sensor made by combination of a light source and a photodetector. For example, the light source may be provided at the characteristic point of the support arm 65 and the photodetector may be provided at the storage position PR of the movable truck 61. When the characteristic point is located at the storage position PR, the optical sensor outputs the ON signal, while if it is not located at the storage position PR, the optical sensor outputs the OFF signal. That is, the processing circuitry 210 determines that, if the ON signal is output, the support arm 65 is in the first case. While if the OFF signal is output, the processing circuitry 210 determines that the support arm 65 is in the second case. By means of this configuration, triggered that the patient P is placed on the top plate 131 and the support arm 65 is withdrawn in order to adjust the position of the reflecting plate 67 in the Z-axis direction, the first video can be switched to the second video. The arrangement of the light source and the detector is not limited only to the above, but the optical sensor may be provided at positions faced with each other by sandwiching the support arm 65 at the storage position PR of the movable truck 61.

The position detector 19 may be mounted on any one of the top plate 131, the reflecting plate 67, and the support arm 65 or the detector 19 may be mounted on a plurality of or all of them. If the detector 19 is mounted on any one of the top plate 131, the reflecting plate 67, and the support arm 65, the processing circuitry 210 preferably proceeds to Step S5 upon determination that any one of the devices 131, 65, and 67 on which the position detectors 19 are mounted has been switched to the second case. In this case, as compared with a case where the detector 19 is mounted on a plurality of or all of the devices 131, 65, and 67, switching to the second projection mode can be made more rapidly. If the detectors 19 are mounted on a plurality of or all of the top plate 131, the reflecting plate 67, and the support arm 65, it is preferable to proceed to Step S5 upon determination that all or a predetermined number of the devices 131, 65 and 67 on which the detector 19 is mounted has been switched to the second case. In this case, as compared with a case where the position detector 19 is mounted on any one of the devices 131, 65, and 67, the switching to the second case can be detected more accurately.

At Step S4, if it is determined that the top plate 131, the reflecting plate 67 or the support arm 65 has been switched from the first case to the second arrangements mode (Step S4: YES), the processing circuitry 210 executes the projection image output function 217 (Step S5). At Step S5, the processing circuitry 210 outputs the second video signal relating to the second video to the projector 100 through the connection circuitry 270. Specifically, first, the processing circuitry 210 finishes output of the first video signal and reads out the image data relating to the second video from the projection image storage circuitry 220. The read-out image data relating to the second image is preferably set in advance in order to instantaneously switch from the first video to the second video. By setting the image data relating to the second video to be read out in advance, reading-out of the image data relating to the second video and switching from the first video to the second video can be smoothly performed automatically. The read-out second video may be set at Step S5 through the input circuitry 36. When the image data relating to the second video is read out, the processing circuitry 210 converts the plurality of frames constituting the image data of the read-out second video to the second video signal by the unit of frame in a time series and outputs it to the projector 100. Here, Step S5 will be described in detail.

As described above, in the first projection mode, the patient P sees the video not through the reflecting plate 67. In the second projection mode, the patient P sees the video through the reflecting plate 67. Thus, if the first video and the second video have the same contents, the patient P who saw the second video feels inversion of the video. The processing circuitry 210 outputs the second video signal in a mode that the patient P does not feel the inversion of the video when the patient P sees the second video. Specifically, the processing circuitry 210 sets a video in which the first video is right-and-left inverted to the second video at Step S5.

Figure 23:
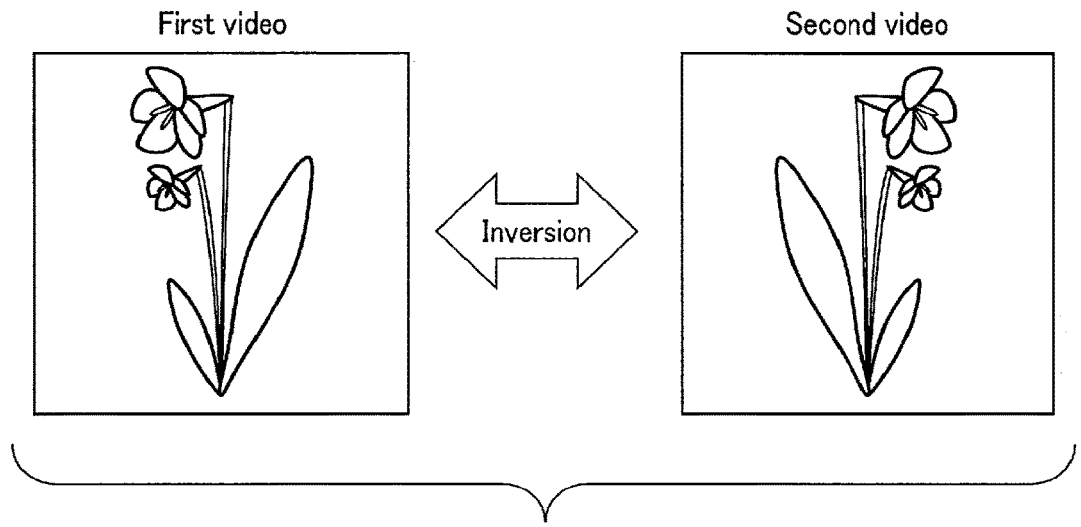
FIG. 23 is a view schematically illustrating a first video and a second video in a horizontally inversion relation with each other.

FIG. 23 is a view schematically illustrating the first video and the second video in the right-and-left inversion relation with each other. As illustrated in FIG. 23, the first video and the second video are the same contents relating to a flower, and the first video and the second video are in the right-and-left inversion relation with each other. The image data of the second video which is right-and-left inverted with respect to the first video is generated by execution by the processing circuitry 210 of the image processing function 215, for example. Specifically, the processing circuitry 210 generates the image data of the second video constituted by a plurality of right-and-left inverted frames by inverting right and left of each of the plurality of frames constituting the image data of the first image. The image data of the second video is preferably generated before proceeding to Step S5 such as a stage before the patient P is placed on the top plate 131, for example. The generated image data of the second video is stored in the projection image storage circuitry 220. In this case, at Step S5, the processing circuitry 210 reads out the image data of the second video stored in the projection image storage circuitry 220, converts the read-out image data of the second video to the second video signal by the unit of frame in a time series, and outputs it to the projector 100 through the connection circuitry 270 on a real time basis. The projector 100 projects the second video corresponding to the second video signal to the movable screen unit 15 by the unit of frame in a time series. The patient P seeing the second video through the reflecting plate 67 can see the second video directed to the same direction as that of the first video.

The right-and-left inversion may be performed on a real time basis at output of the second video signal. For example, at step S5, the processing circuitry 210 reads out the image data of the first video from the projection image storage circuitry 220, right-and-left invert a plurality of frames constituting the read-out image data of the first video in a time order, convert the right-and-left inverted frame to the second video signal on a real time basis, and output it to the projector 100 through the connection circuitry 270. As a result, without generating the image data of the inverted second video in advance, the second video can be output to the projector 100.

In the aforementioned example, the inversion is described to be the right-and-left inversion, but the processing circuitry 210 may rotate or invert the first video in a direction according to an attitude of the patient lying on the top plate 131. For example, if the patient is lying in a lateral position on the top plate 131, the processing circuitry 210 preferably generates the second video by rotating the first video around an image center point by 90 degrees. Depending on arrangement of the reflecting plate 67 interposed between the screen 63 and the patient P, the processing circuitry 210 preferably generates the second video by vertically inverting the first video.

If the second video and the first video have the same contents, even if the first projection mode is switched to the second projection mode, the first video is continuously projected to the movable screen unit 15 as the second video. The patient P needs to prepare for being placed on the top plate 131 at switching from the first projection mode to the second projection mode and thus, the patient cannot see the video projected to the movable screen unit 15 in some cases. In this case, the patient P feels a temporal gap between the first video and the second video when the patient P sees the second video.

Therefore, if the second video and the first video have the same contents, the processing circuitry 210 according to this embodiment adjusts a playback start frame of the second video so that the patient P does not feel the temporal gap between the second video and the first video.

Figure 24:
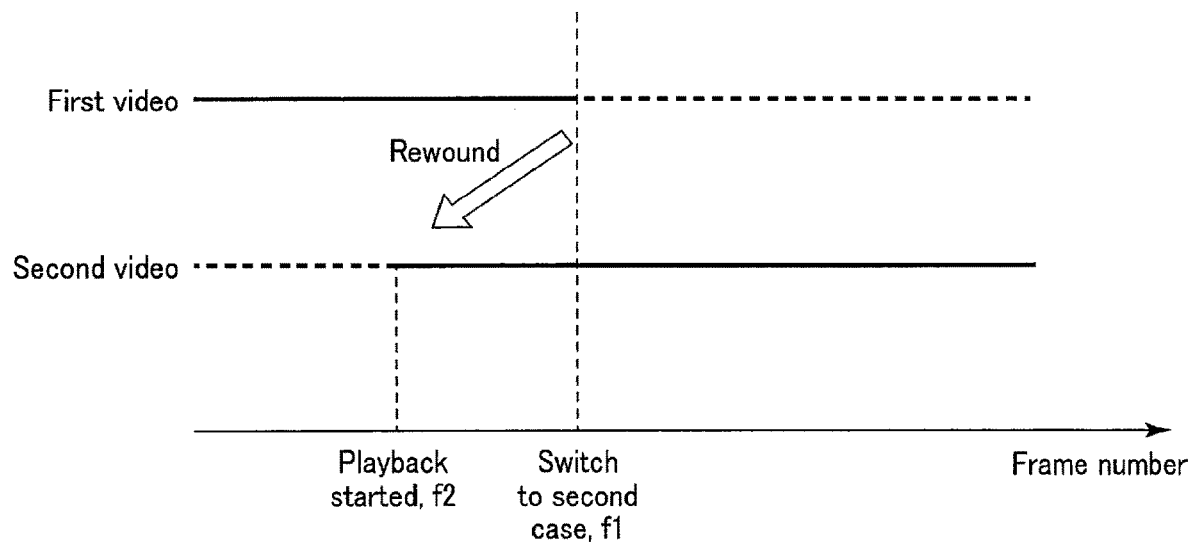
FIG. 24 is a diagram illustrating adjustment processing of a playback start frame of the second video.

FIG. 24 is a view illustrating adjustment processing of the playback start frame of the second video. It is assumed that the first video and the second video have the same contents, and the video signal of the same frame shows the same contents. As illustrated in FIG. 24, in the first projection mode, the processing circuitry 210 outputs the first video signal relating to the first video by the unit of frame in a time series. When the switching of the first case to the second case is determined (Step S4: YES), the processing circuitry 210 switches the output signal to the projector 100 from the first video signal to the second video signal.

Specifically, when the switching of the first case to the second case is determined (Step S4: YES), the processing circuitry 210 specifies a frame number F1 of the first video output at the switching. Then, the processing circuitry 210 searches the plurality of frames constituting the image data relating to the second video and specifies a frame number F2 rewound by a predetermined number from the specified frame number F1. The specified frame number F2 is set as the reproduction start frame of the second video. The number of rewound frames is preferably set arbitrarily in accordance with time for which the patient P is expected not to see the movable screen unit 15. Then, the processing circuitry 210 outputs the second video signal from the frame number F2 in a time series to the projector 100. As a result, since the second video is projected to the movable screen unit 15 from the frame rewound by the predetermined number from the frame at the switching, the patient can see the second video without feeling the temporal gap.

The second video has the same contents as those of the first video and is not limited only to the video inverted or rotated with respect to the first video. The contents of the first video and the second video may be different.

FIG. 25 is a view schematically illustrating the first video and the second video relating to different contents. As illustrated in FIG. 25, the first video has the contents relating to a flower, while the second video has the contents relating to a cake. If the second video has the contents different from those of the first video, the patient does not feel that the second video is right-and-left inversion of the first image when the patient sees the second video. Thus, since the second video signal is a video signal of the video having the contents different from those of the first video, the sense of discomfort caused the right-and-left inversion can be avoided.

When Step S5 is executed, the processing circuitry 210 waits for an end instruction of the video projection (Step S6). When the end instruction of the video projection has not been given (Step S6: NO), the processing circuitry 210 repeats Step S5 and Step S6 and repeatedly outputs the second video signal for projecting the second video on the movable screen unit 15 to the projector 100. The end instruction of the video projection is given by an instruction by the medical staff, for example, through the input circuitry 250. For example, after MR imaging is finished and the top plate 131 on which the patient is placed is retreated to the outside of the bore 53, the medical staff inputs the end instruction of the video projection. When the end instruction is input by the medical staff or the like through the input circuitry 250 (Step S6: YES), the processing circuitry 210 finishes the output of the second video signal to the projector 100.

The description on the image projection processing executed by the processing circuitry 210 in accordance with the image projection program according to this embodiment has been made above.

It was described that the position detector 19 for detecting a height of the top plate 131 for discriminating switching of the top plate 131 to the second case is provided. However, this embodiment is not limited to that. For example, the position detector 19 for detecting a position of the top plate 131 relating to the Z-axis direction (horizontal direction) may be provided. The position of the top plate 131 relating to the Z-axis direction may be regulated by a position of any characteristic point of the top plate 131 but it is preferably regulated to a projector side end portion, for example. In this case, a reference value for discriminating between the first case and the second case may be set to a position of a couch-side end portion of the gantry housing 51 in the Z-axis direction.

The position detector 19 may be a distance sensor for measuring a distance between it and the screen 63 by using infrared rays or the like. The position detector 19 may be provided at any position as long as the distance in the first case is different from the distance in the second case, but it is preferably provided in the eh vicinity of the projector 100, for example. A reference value for discriminating between the first case and the second case is preferably set to a distance when the screen 63 is disposed at the couch-side end portion in the first case. As a result, the processing circuitry 210 determines the stage before the screen 63 is inserted into the bore 53 as the first case and determines the state where the screen 63 is inserted into the bore 53 as the second case based on the position signal from the position detector 19.

The processing circuitry 210 may execute switching between the first video and the second video triggered the start instruction of the MR examination through the input circuitry 36 of the console 27. Moreover, the processing circuitry 210 may execute switching between the first video and the second video triggered mounting of a dedicated coil such as a head-part coil to the patient fixture 137 or the like. Moreover, the processing circuitry 210 may switch the second video at each switching between each of imaging protocols configuring the MR examination.

As described above, the magnetic resonance imaging system 1 according to this embodiment has the gantry 11, the couch 13, the movable screen unit 15, and the processing circuitry 210. The gantry 11 is for magnetic resonance imaging and has the bore 53. The couch 13 movably supports the top plate 131. The movable screen unit 15 is disposed in the bore 53 and has the screen 63 to which the video from the projector 100 is projected, the reflecting plate 67 for reflecting the video projected to the screen 63, and the support arm 65 to support the reflecting plate 67. The processing circuitry 210 has the projection image output function 217. By execution of the projection image output function 217, the processing circuitry 210 outputs the first video signal to the projector 100 before the switching between the first case and the second case is made and outputs the second video signal to the projector 100 after the switching is made. The first case is where the observer watches the video projected on the screen 63 not through the reflecting plate 67. The second case is where the observer watches the video projected on the screen 63 through the reflecting plate 67.

By means of the aforementioned configuration, the magnetic resonance imaging system 1 supplies the second video signal different from the first video signal in the first projection mode to the projector 100, triggered the switching between the first projection mode and the second projection mode. As a result, the sense of discomfort of the patient P to the video caused by the switching between the first projection mode and the second projection mode can be solved. By automatically recognizing the switching between the first projection mode and the second projection mode, a labor of the switching between the first video signal and the second video signal can be reduced.

Thus, according to this embodiment, habitability in the bore 53 of the gantry 11 can be improved.

(Variation)

In the aforementioned embodiment, the magnetic resonance imaging system 1 is assumed to be equipped with the projector control apparatus 200 for controlling the projector 100 separately from the imaging control unit 17. However, this embodiment is not limited to that. Hereinafter the magnetic resonance imaging system according to a variation will be described. In the following explanation, the constituent elements having the substantially same function as that of this embodiment are given the same reference numerals and duplication explanation will be given when it is only necessary.

FIG. 26 is a diagram illustrating configuration of the magnetic resonance imaging system 2 according to the variation. As illustrated in FIG. 26, the magnetic resonance imaging system 2 according to the variation has the magnetic resonance imaging apparatus 10 and the projector 100. The magnetic resonance imaging apparatus 10 has an imaging control unit 18 in addition to the gantry 11, the couch 13, and the movable screen unit 15. The imaging control unit 18 controls the projector 100 in addition to the gantry 11 and the couch 13.

Figure 27:
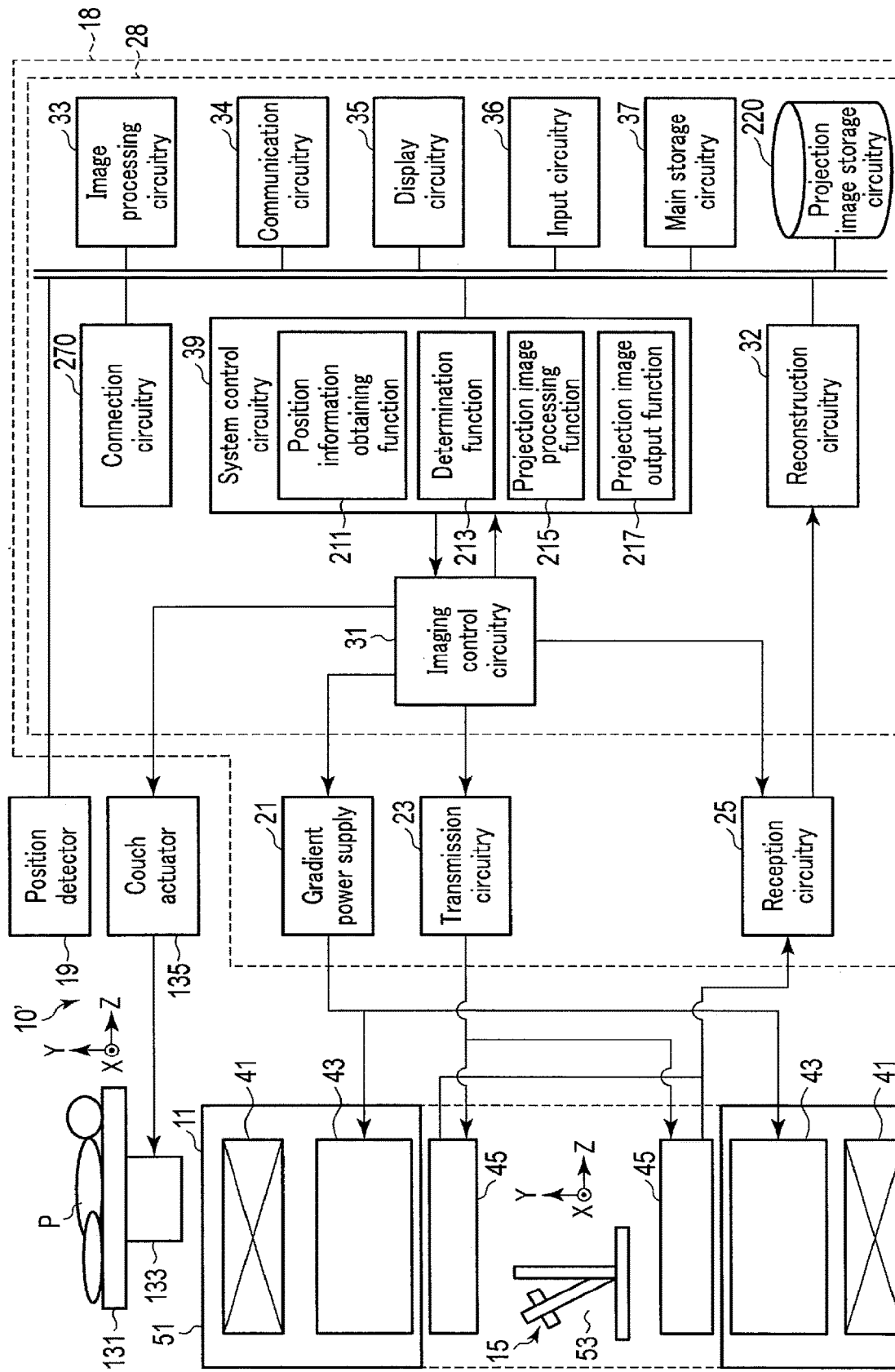
FIG. 27 is a diagram illustrating configuration of the magnetic resonance imaging apparatus according to a variation.

FIG. 27 is a diagram illustrating configuration of the magnetic resonance imaging apparatus 10 according to the variation. As illustrated in FIG. 27, the magnetic resonance imaging apparatus 10 has the gantry 11, the couch 13, the movable screen unit 15, the imaging control unit 18, and the position detector 19. The imaging control unit 18 has the gradient power supply 21, the transmission circuitry 23, the reception circuitry 25, and a console 28. The console 28 has the imaging control circuitry 31, the reconstruction circuitry 32, the image processing circuitry 33, the communication circuitry 34, the display circuitry 35, the input circuitry 36, the main storage circuitry 37, a system control circuitry 39, the projection image storage circuitry 220, and the connection circuitry 270. The imaging control circuitry 31, the reconstruction circuitry 32, the image processing circuitry 33, the communication circuitry 34, the display circuitry 35, the input circuitry 36, the main storage circuitry 37, the system control circuitry 39, the projection image storage circuitry 220, and the connection circuitry 270 are communicably connected to each other via a bus.

The connection circuitry 270 is an interface circuit for supplying the image signal to the projector 100 via wire, not shown, or wirelessly. The system control circuitry 39 realizes the position information obtaining function 211, the determination function 213, the projection image processing function 215, and the projection image output function 217 provided in the projector control apparatus 200 according to this embodiment in addition to the function similar to the system control circuitry 38 according to this embodiment. The information obtaining function 211, the determination function 213, the projection image processing function 215, and the projection image output function 217 are executed by reading the image projection program according to this embodiment stored in the main storage circuitry 37 and by developing it to the memory, for example. Since each of the functions 211, 213, 215, and 217 is similar to the aforementioned embodiment, the explanation will be omitted.

As described above, according to at least one embodiment, the magnetic resonance imaging system, the magnetic resonance imaging apparatus, and the video projecting program capable of improving habitability in the bore of the gantry can be provided.

By means of the aforementioned configuration, the video signal can be supplied from the console 27 to the projector 100. Moreover, in the console 27, the position information obtaining function 211, the determination function 213, the video processing function 215, and the video output function 217 can be executed. Thus, the magnetic resonance imaging system 2 according to the variation can be regarded to have simpler configuration than the magnetic resonance imaging system 1 according to this embodiment.

The video shown to the patient or the like in the aforementioned embodiment is described to be projected from the projector 100 to the movable screen unit 15. However, this embodiment is not limited to that. For example, in the variation, a display device may be provided instead of the projector 100. The display device is provided at a position where the patient or the like placed on the top plate 131 can visually recognize the video displayed on the display device through the reflecting plate 67. For example, the display device is preferably mounted on the wall 500 between the examination room 300 and the control room 400 illustrated in FIG. 3. In this case, the screen 63 is removed from the movable screen unit 15. As a result, the patient or the like placed on the top plate 131 can see the video displayed on the display device mounted on the wall 500 through the reflecting plate 67.

By means of the aforementioned configuration, the processing circuitry 210 according to the variation outputs the first video signal relating to the first video in a first case where the video displayed by the display device is shown to the patient or the like not through the reflecting plate 67 and output the second video signal relating to the second video in a second case where the video displayed by the display device is shown to the patient or the like through the reflecting plate 67. Therefore, even if at least either one of the projector 100 and the screen 63 is not provided, the magnetic resonance imaging system 1 according to the variation can switch the video shown to the patient or the like between the first case and the second case.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image diagnosis system, comprising:
a gantry for medical imaging, the gantry having a bore;
a top plate;
a couch configured to movably support the top plate;
a display unit disposed in the bore of the gantry and configured to display an output image;
a reflecting plate configured to reflect the output image output from the display unit, the reflecting plate being provided in front of the display unit;
a detector configured to detect a position of the reflecting plate, the position being associated with a rotation angle of the reflecting plate and/or a presence of the reflecting plate; and
processing circuitry configured to:
determine, based on the detected position of the reflecting plate, whether switching between a first projection mode and a second projection mode is required, the first projection mode allowing the output image displayed on the display unit to be viewed by an observer from an outside of the bore of the gantry not through the reflecting plate, and the second projection mode allowing the output image displayed on the display unit to be viewed by an observer placed on the top plate through the reflecting plate, wherein the processing circuitry determines that the first projection mode is required in a case where the detected position of the reflecting plate indicates a first rotation angle, and the processing circuitry determines that the second projection mode is required in a case where the detected position of the reflecting plate indicates a second rotation angle, the first and second rotation angles being angles formed by the reflecting plate and a direction along the bore of the gantry, the first rotation angle being smaller than the second rotation angle, and
switch the output image between a first output image and a second output image that is an inverted image of the first output image based on the determination that switching between the first projection mode and the second projection mode is required, the first output image being displayed on the display unit to be viewed not through the reflecting plate in the first projection mode, and the second output image being displayed on the display unit in place of the first output image to be viewed through the reflecting plate in the second projection mode.

2. The medical image diagnosis system according to claim 1, wherein
the processing circuitry is further configured to switch the output image between playing a first video including a plurality of first output images and playing a second video including a plurality of second output images that represent contents identical to contents of the plurality of first output images, and to replay a corresponding portion of the contents of the first video or the second video at switching.

3. The medical image diagnosis system according to claim 1, wherein
the first output image is to be displayed on the display unit when the observer is outside the bore, and the second output image is to be displayed on the display unit when the observer is placed on the top plate.

4. The medical image diagnosis system according to claim 1, wherein the display unit includes a screen disposed in the bore of the gantry and configured to display the first and second output images which are provided by an image output device.

5. A medical image diagnosis system, comprising:
a gantry for medical imaging, the gantry having a bore;
a top plate;
a couch configured to movably support the top plate;
an image output device configured to output an output image;
a screen disposed in the bore of the gantry and configured to display the output image provided by the image output device;
a reflecting plate configured to reflect the output image displayed on the screen, the reflecting plate being provided in front of the screen;
a detector configured to detect a position of the reflecting plate, the position being associated with a rotation angle of the reflecting plate and/or a presence of the reflecting plate; and
processing circuitry configured to
determine, based on the detected position of the reflecting plate, whether switching between a first projection mode and a second projection mode is required, the first projection mode allowing the output image displayed on the screen to be viewed by an observer from an outside of the bore of the gantry not through the reflecting plate, and the second projection mode allowing the output image displayed on the screen to be viewed by an observer placed on the top plate through the reflecting plate, wherein the processing circuitry determines that the first projection mode is required in a case where the detected position of the reflecting plate indicates a first rotation angle, and the processing circuitry determines that the second projection mode is required in a case where the detected position of the reflecting plate indicates a second rotation angle, the first and second rotation angles being angles formed by the reflecting plate and a direction along the bore of the gantry, the first rotation angle being smaller than the second rotation angle, and
control the image output device to switch the output image between a first output image and a second output image that is an inverted image of the first output image based on the determination that switching between the first projection mode and the second projection mode is required, the first output image being displayed on the screen to be viewed not through the reflecting plate in the first projection mode, and the second output image being displayed on the screen in place of the first output image to be viewed through the reflecting plate in the second projection mode.

6. The medical image diagnosis system according to claim 5, wherein
the processing circuitry is further configured to switch the output image between playing a first video including a plurality of first output images and playing a second video including a plurality of second output images that represent contents identical to contents of the plurality of first output images, and to replay a corresponding portion of the contents of the first video or the second video at switching.

7. The medical image diagnosis system according to claim 5, wherein
the first output image is to be displayed on the screen when the observer is outside the bore, and the second output image is to be displayed on the screen when the observer is placed on the top plate.

* * * * *